United States Patent
Fukazawa et al.

(10) Patent No.: US 10,849,482 B2
(45) Date of Patent: Dec. 1, 2020

(54) ENDOSCOPIC SYSTEM, IMAGE PROCESSING APPARATUS, AND IMAGE PROCESSING METHOD

(71) Applicant: SONY CORPORATION, Tokyo (JP)

(72) Inventors: Kentaro Fukazawa, Tokyo (JP); Takeshi Miyai, Kanagawa (JP); Kenta Yamaguchi, Kanagawa (JP); Yukihiro Nakamura, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 469 days.

(21) Appl. No.: 15/519,980

(22) PCT Filed: Jan. 26, 2016

(86) PCT No.: PCT/JP2016/000362
§ 371 (c)(1),
(2) Date: Apr. 18, 2017

(87) PCT Pub. No.: WO2016/125450
PCT Pub. Date: Aug. 11, 2016

(65) Prior Publication Data
US 2017/0367558 A1     Dec. 28, 2017

(30) Foreign Application Priority Data

Feb. 5, 2015   (JP) .................................. 2015-021078

(51) Int. Cl.
| | |
|---|---|
| *A61B 1/06* | (2006.01) |
| *A61B 1/04* | (2006.01) |
| *A61B 1/00* | (2006.01) |
| *H04N 5/225* | (2006.01) |

(52) U.S. Cl.
CPC ........ *A61B 1/00009* (2013.01); *A61B 1/0623* (2013.01); *A61B 1/0661* (2013.01);
(Continued)

(58) Field of Classification Search
USPC ......................................................... 600/160
See application file for complete search history.

(56) References Cited

U.S. PATENT DOCUMENTS

| | | | | |
|---|---|---|---|---|
| 6,088,612 A | * | 7/2000 | Blair | .................. A61B 1/00048 250/559.05 |
| 6,975,898 B2 | * | 12/2005 | Seibel | ................ A61B 1/00048 600/473 |

(Continued)

FOREIGN PATENT DOCUMENTS

| | | |
|---|---|---|
| JP | 1-160526 A | 6/1989 |
| JP | 2001-224549 A | 8/2001 |

(Continued)

OTHER PUBLICATIONS

International Search Report dated Apr. 8, 2016 in PCT/JP2016/000362 filed Jan. 26, 2016.

(Continued)

*Primary Examiner* — John P Leubecker
*Assistant Examiner* — Shankar Raj Ghimire
(74) *Attorney, Agent, or Firm* — Xsensus LLP

(57) ABSTRACT

An endoscopic system including an endoscope device that outputs image data, an illumination device that illuminates a body of a patient, and circuitry that obtains, from the image data, at least two frames each captured with a different illumination state, generate, from at least two obtained frames, a composite image that has a reduced specular reflection light component with respect to at least one of the obtained frames, and generate a video signal including the composite image.

18 Claims, 14 Drawing Sheets

(52) U.S. Cl.
CPC .......... *A61B 1/0669* (2013.01); *A61B 1/0676* (2013.01); *A61B 1/0684* (2013.01); *H04N 5/2256* (2013.01)

(56) References Cited

U.S. PATENT DOCUMENTS

| | | | | |
|---|---|---|---|---|
| 9,912,847 B1* | 3/2018 | Yuan | ...................... | H04N 5/225 |
| 2003/0120156 A1* | 6/2003 | Forrester | ................ | A61B 1/042 |
| | | | | 600/473 |
| 2006/0072843 A1* | 4/2006 | Johnston | ................. | G06K 9/20 |
| | | | | 382/254 |
| 2008/0165266 A1* | 7/2008 | Jenkins | ................ | G06F 3/0418 |
| | | | | 348/333.01 |
| 2010/0103516 A1* | 4/2010 | McKnight | ............... | A63F 13/06 |
| | | | | 359/465 |
| 2011/0305388 A1* | 12/2011 | Wedi | ....................... | G06T 5/005 |
| | | | | 382/165 |
| 2012/0147165 A1* | 6/2012 | Yoshino | ............. | H04N 5/23212 |
| | | | | 348/65 |
| 2012/0218437 A1* | 8/2012 | Hermary | .............. | G01B 11/245 |
| | | | | 348/222.1 |
| 2014/0293091 A1* | 10/2014 | Rhoads | .................... | G01J 3/513 |
| | | | | 348/234 |
| 2016/0187199 A1* | 6/2016 | Brunk | .................... | G01J 3/2823 |
| | | | | 348/89 |

FOREIGN PATENT DOCUMENTS

| | | |
|---|---|---|
| JP | 2006-142003 A | 6/2006 |
| JP | 2012-125293 A | 7/2012 |
| JP | 2012-231422 A | 11/2012 |

OTHER PUBLICATIONS

Office Action dated Nov. 16, 2017 in corresponding Japanese Patent Application No. 2015-021078, 8 pages.

* cited by examiner

[Fig. 1]
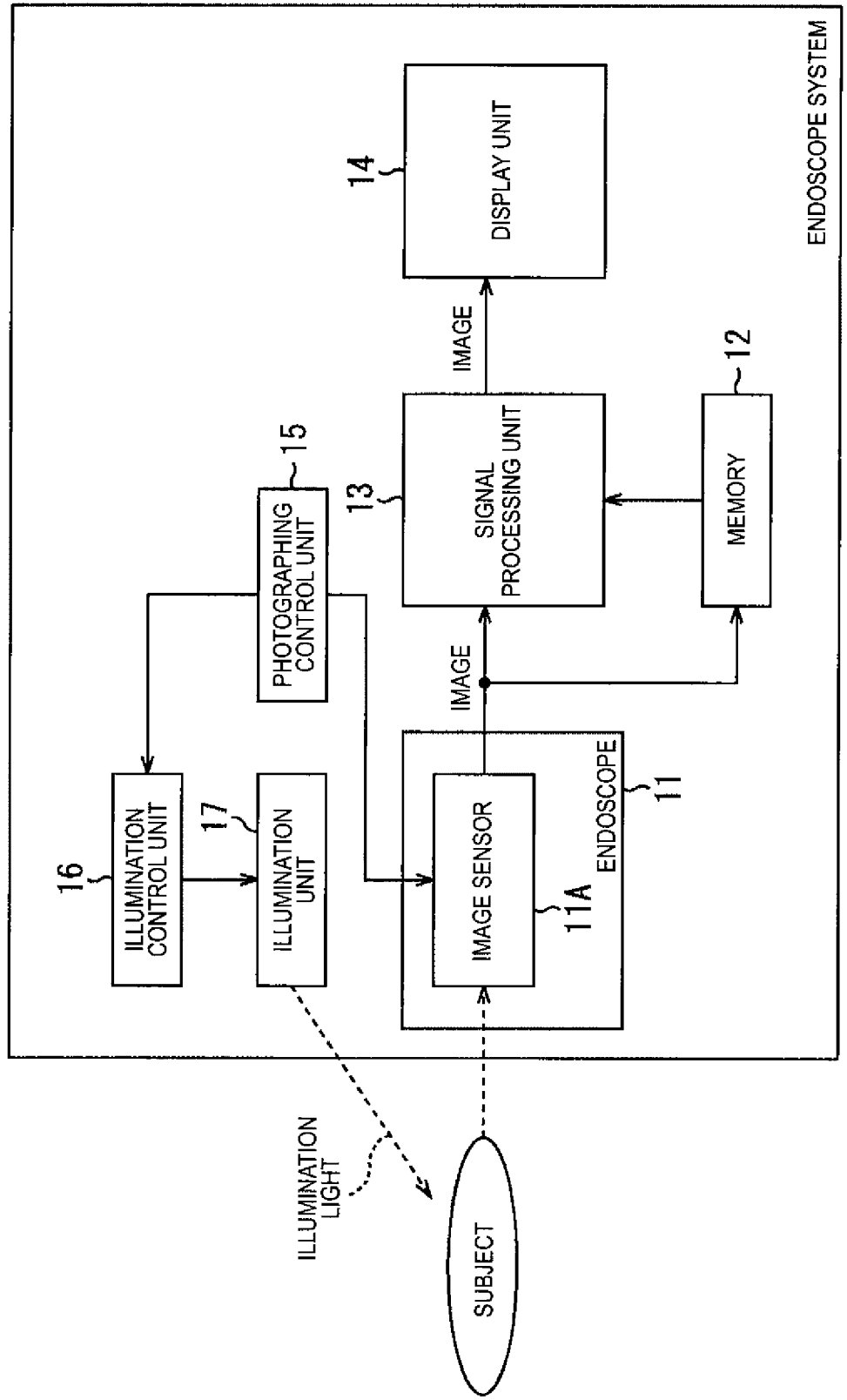

[Fig. 2]
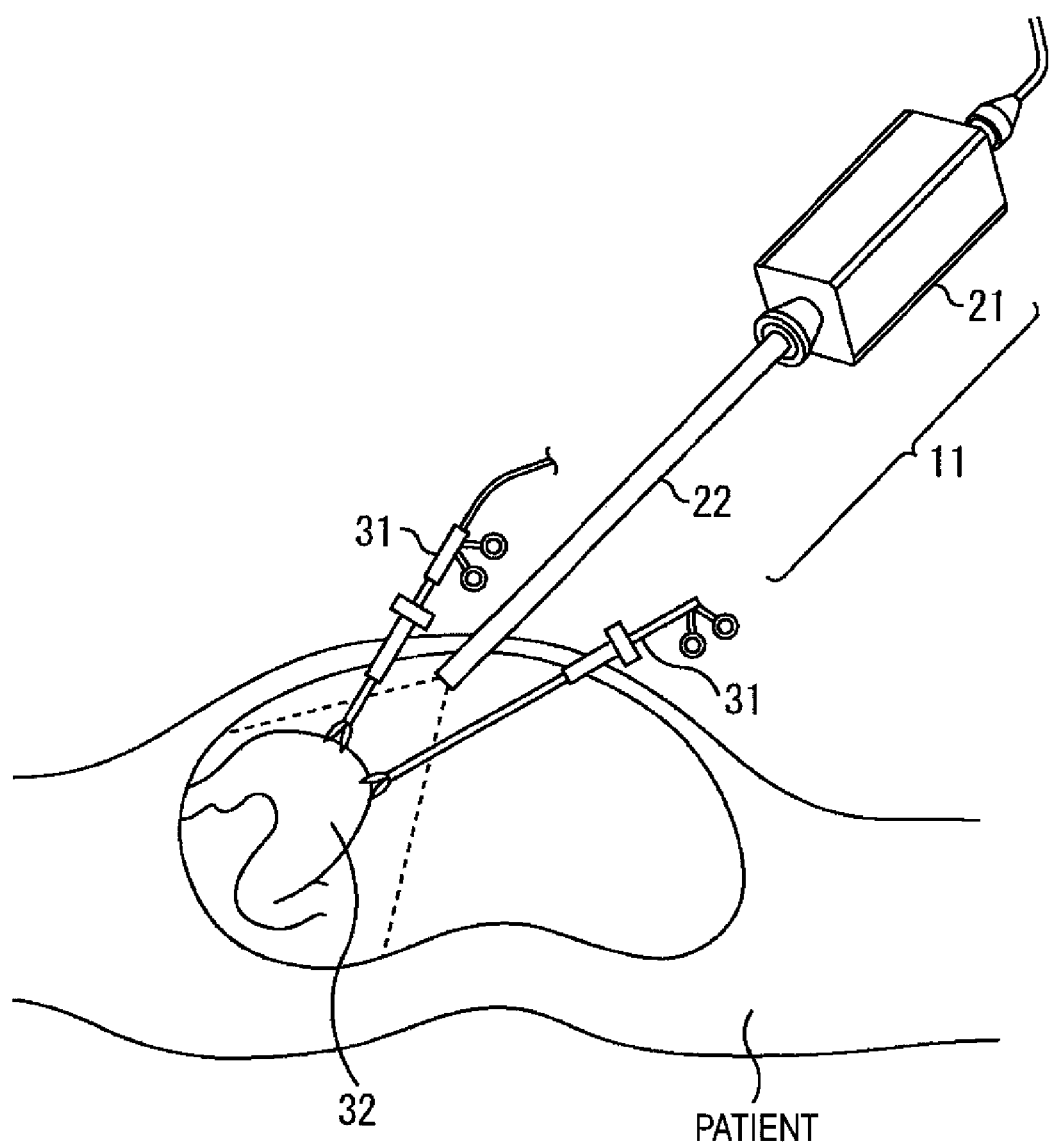

[Fig. 3]
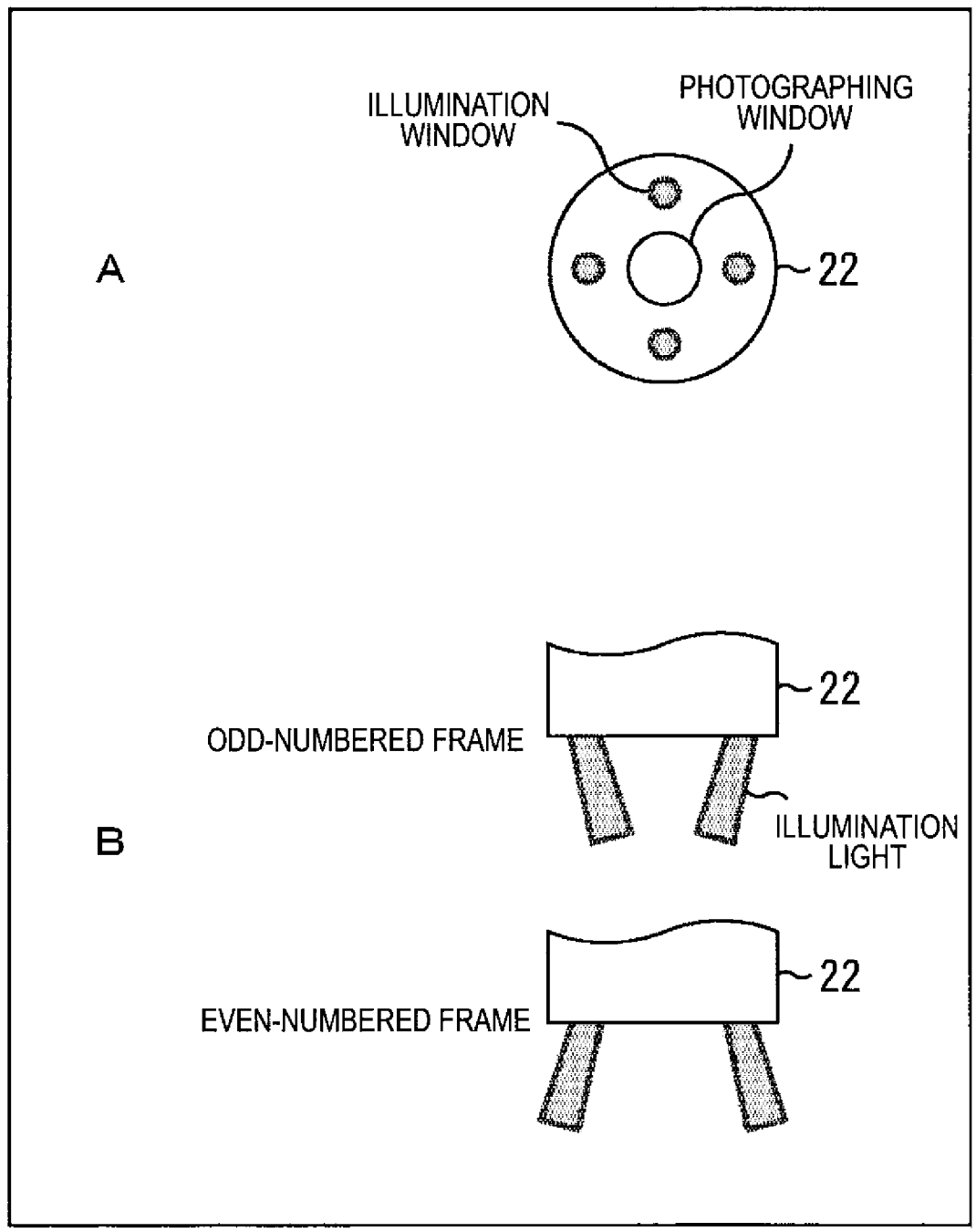

[Fig. 4]
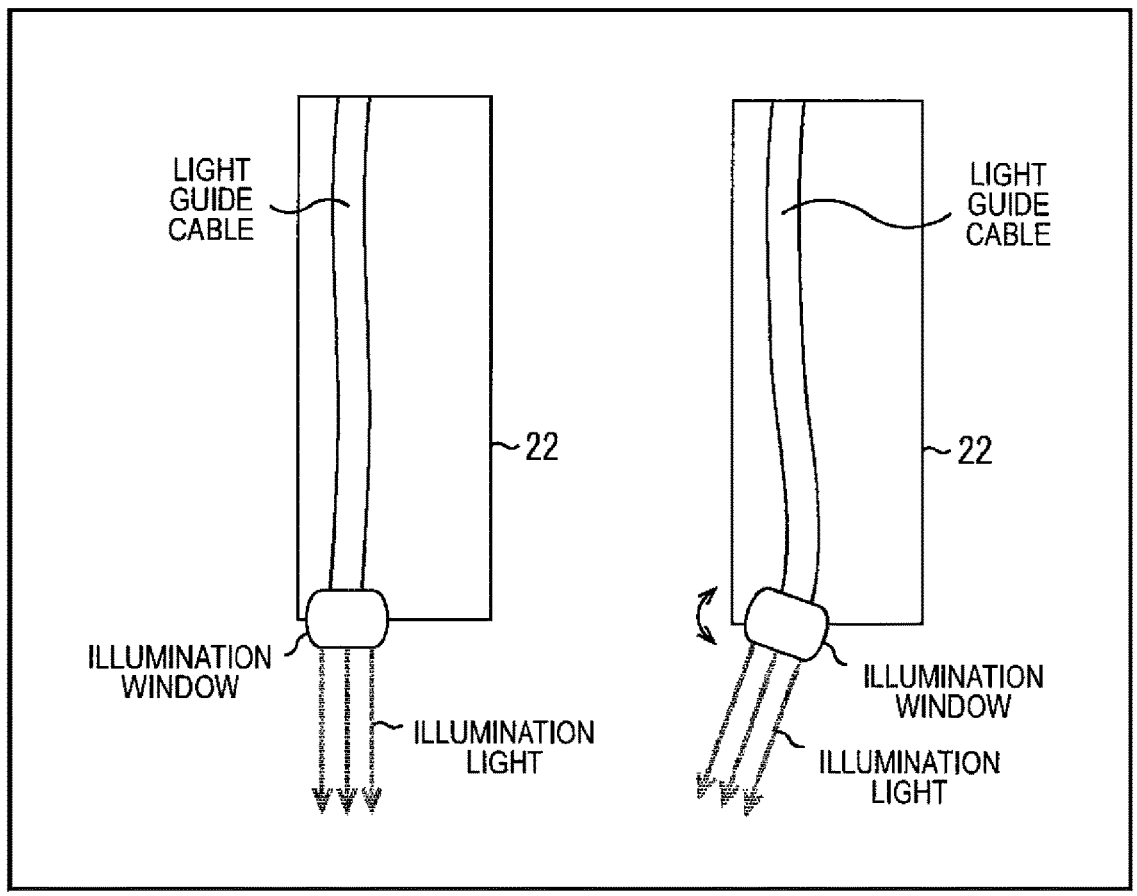

[Fig. 5]
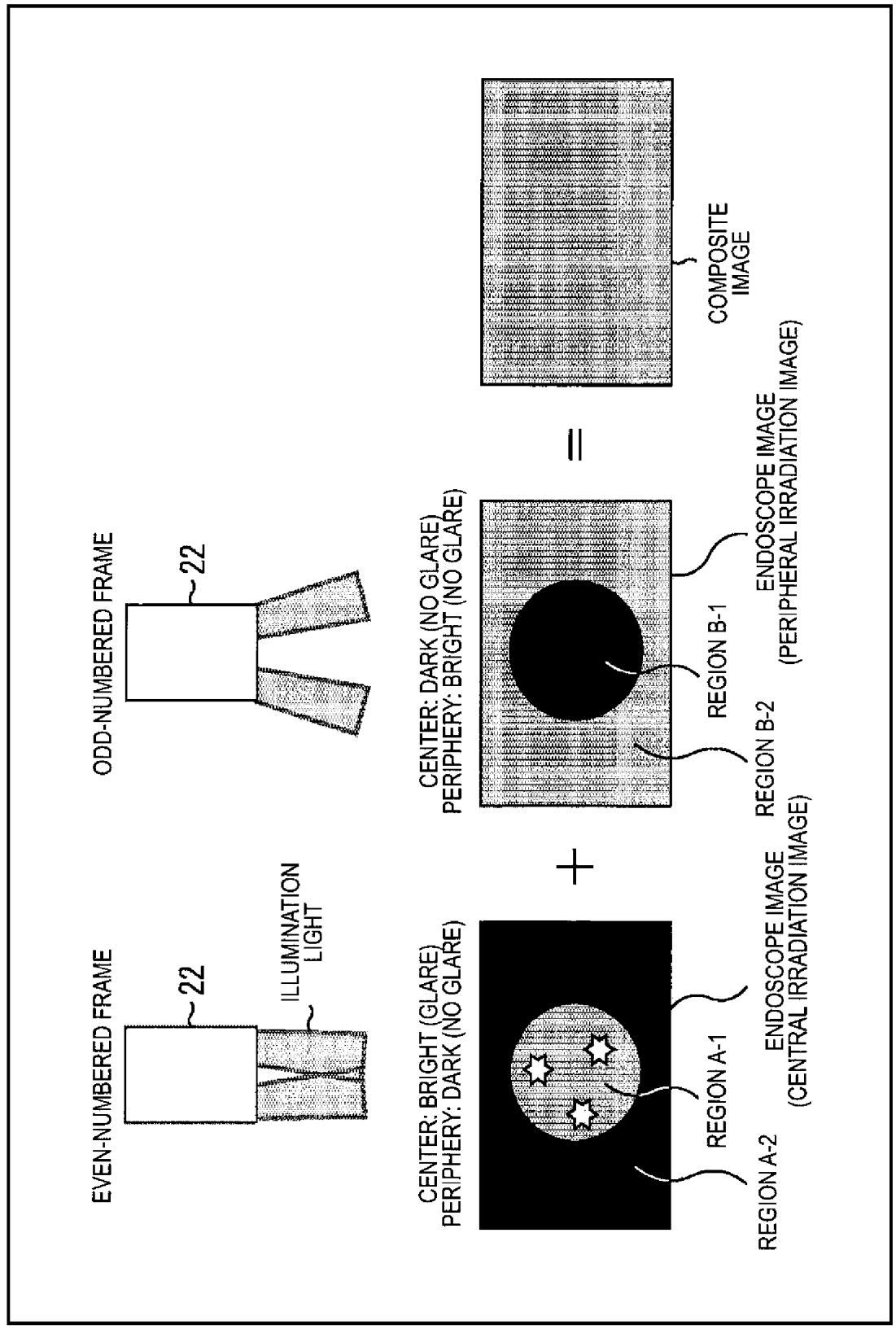

[Fig. 6]
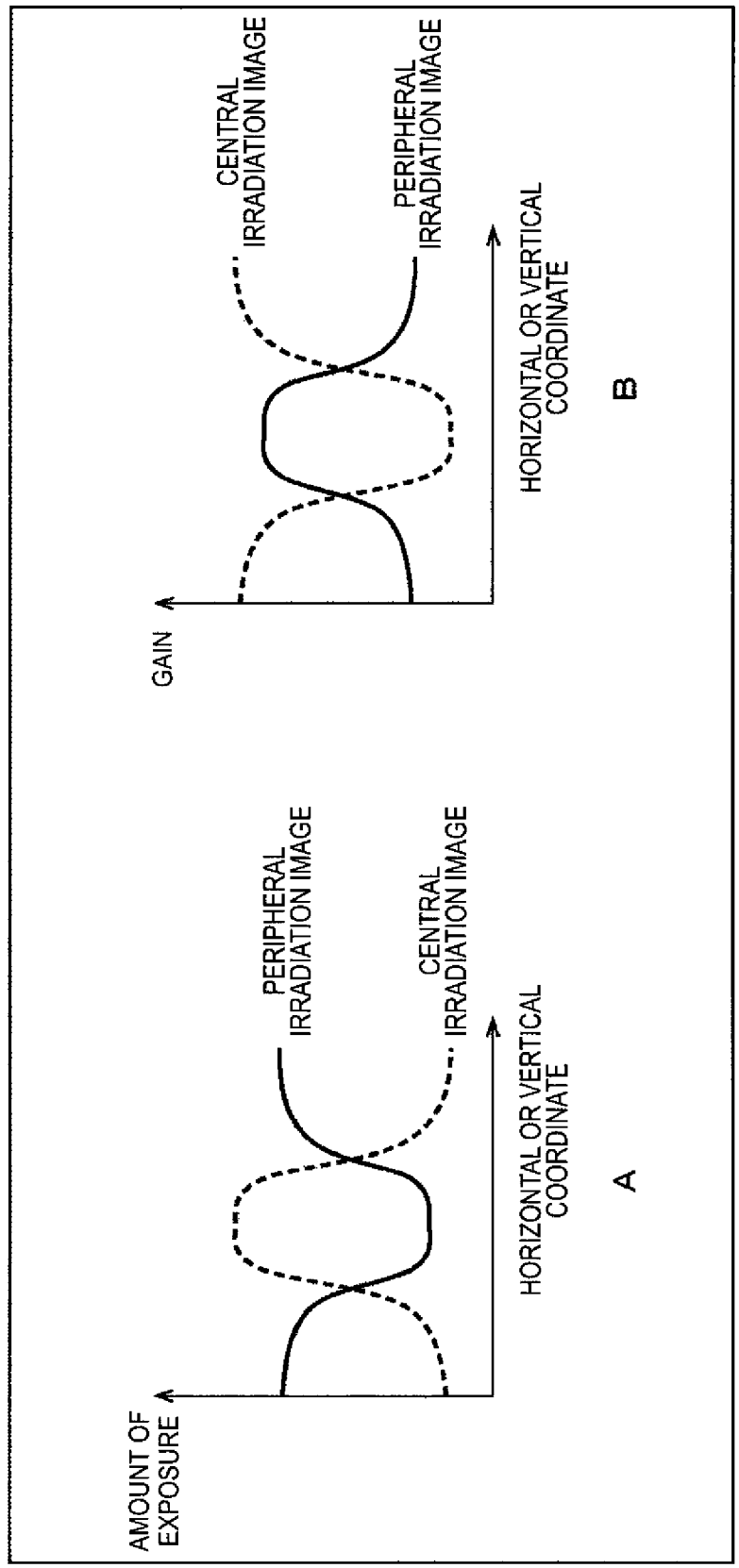

[Fig. 7]
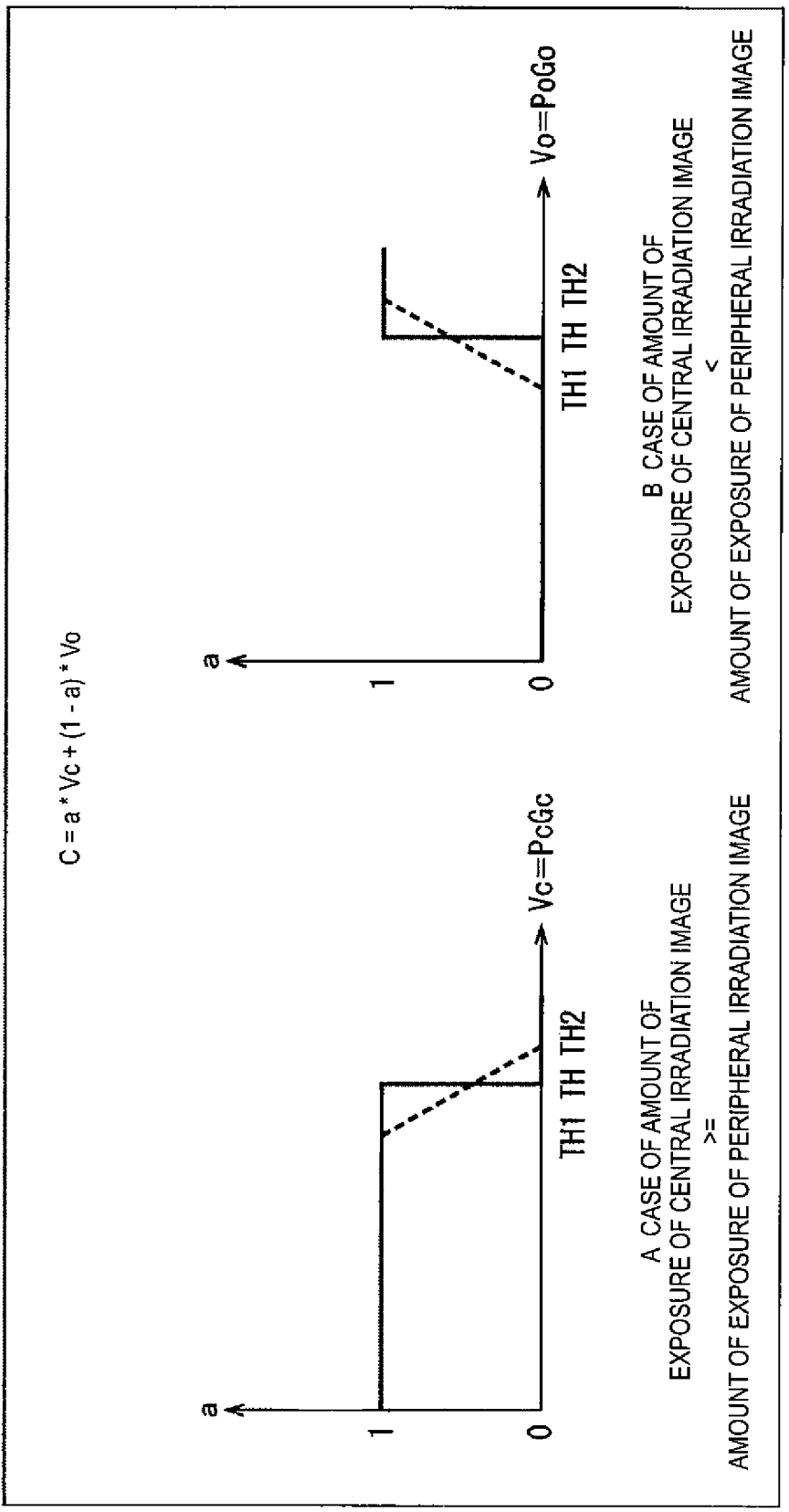

[Fig. 8]
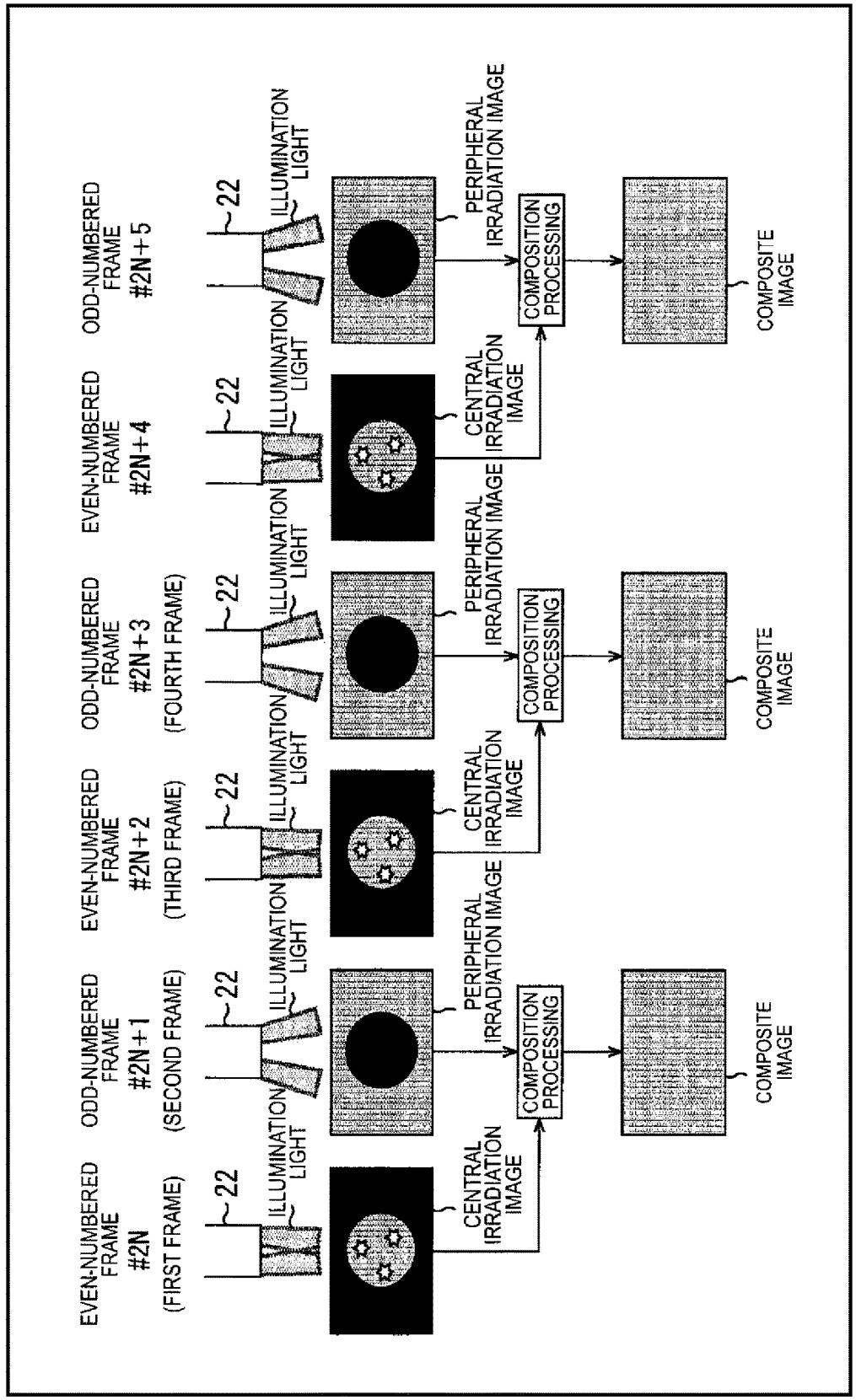

[Fig. 9]
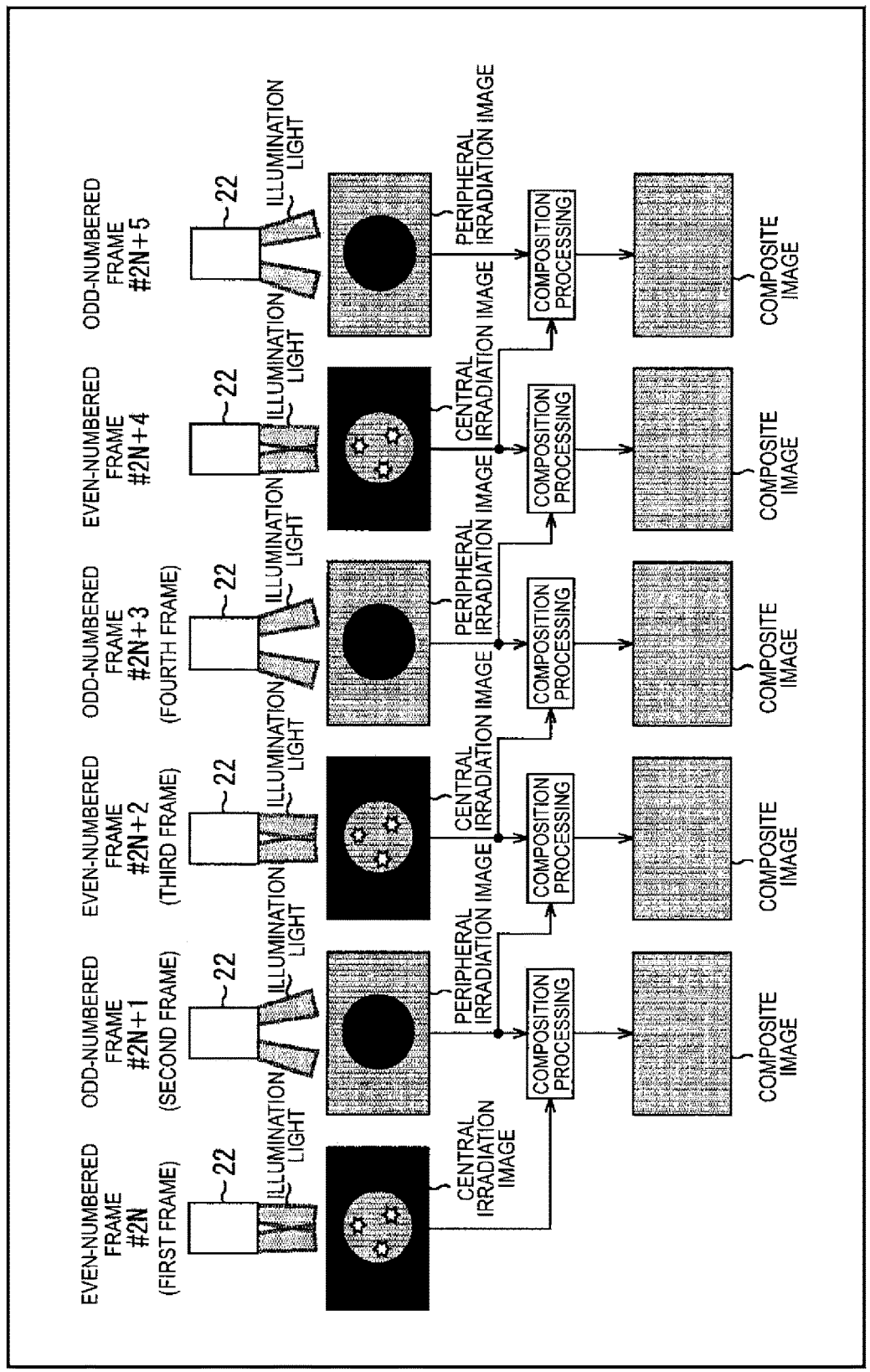

[Fig. 10]
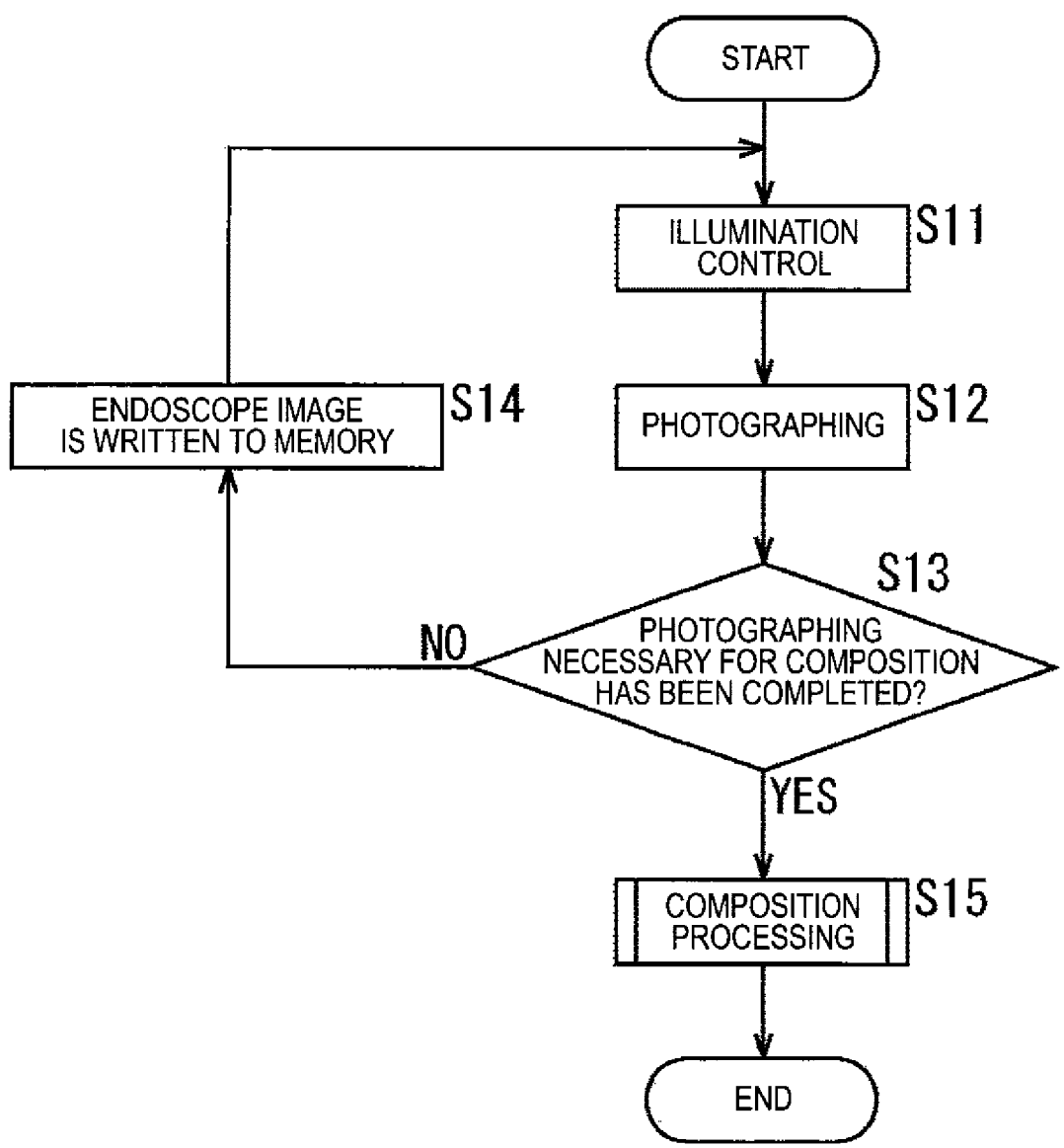

[Fig. 11]
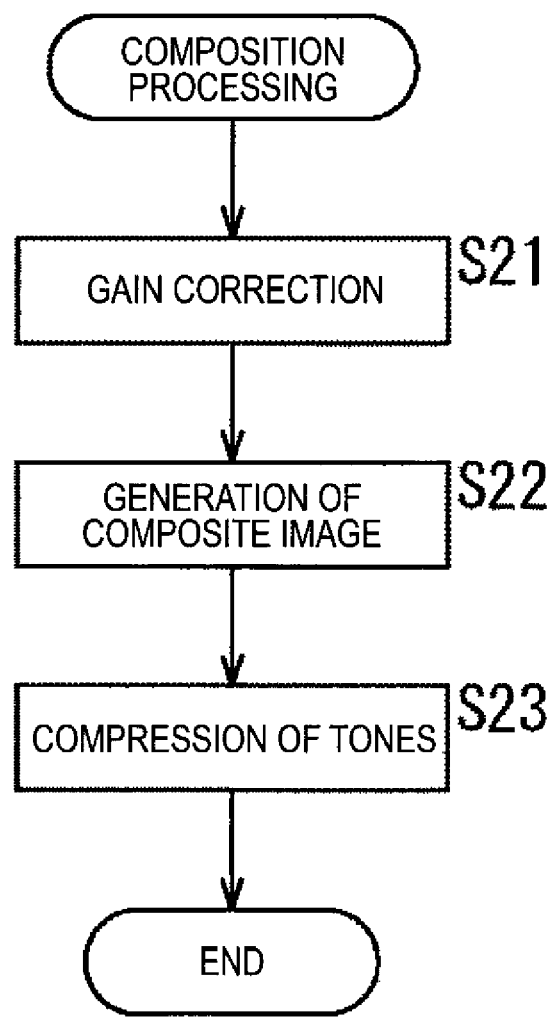

[Fig. 12]
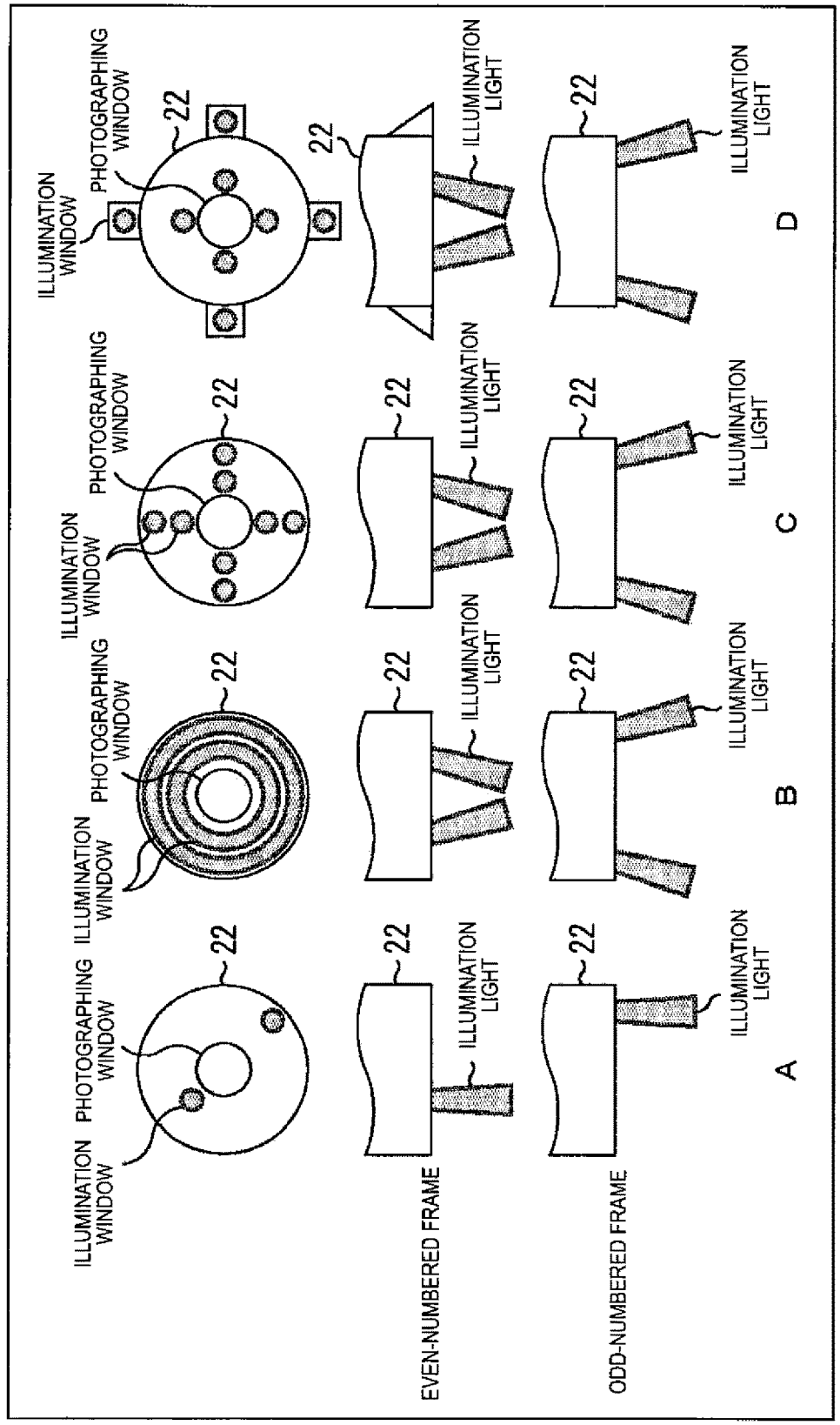

[Fig. 13]
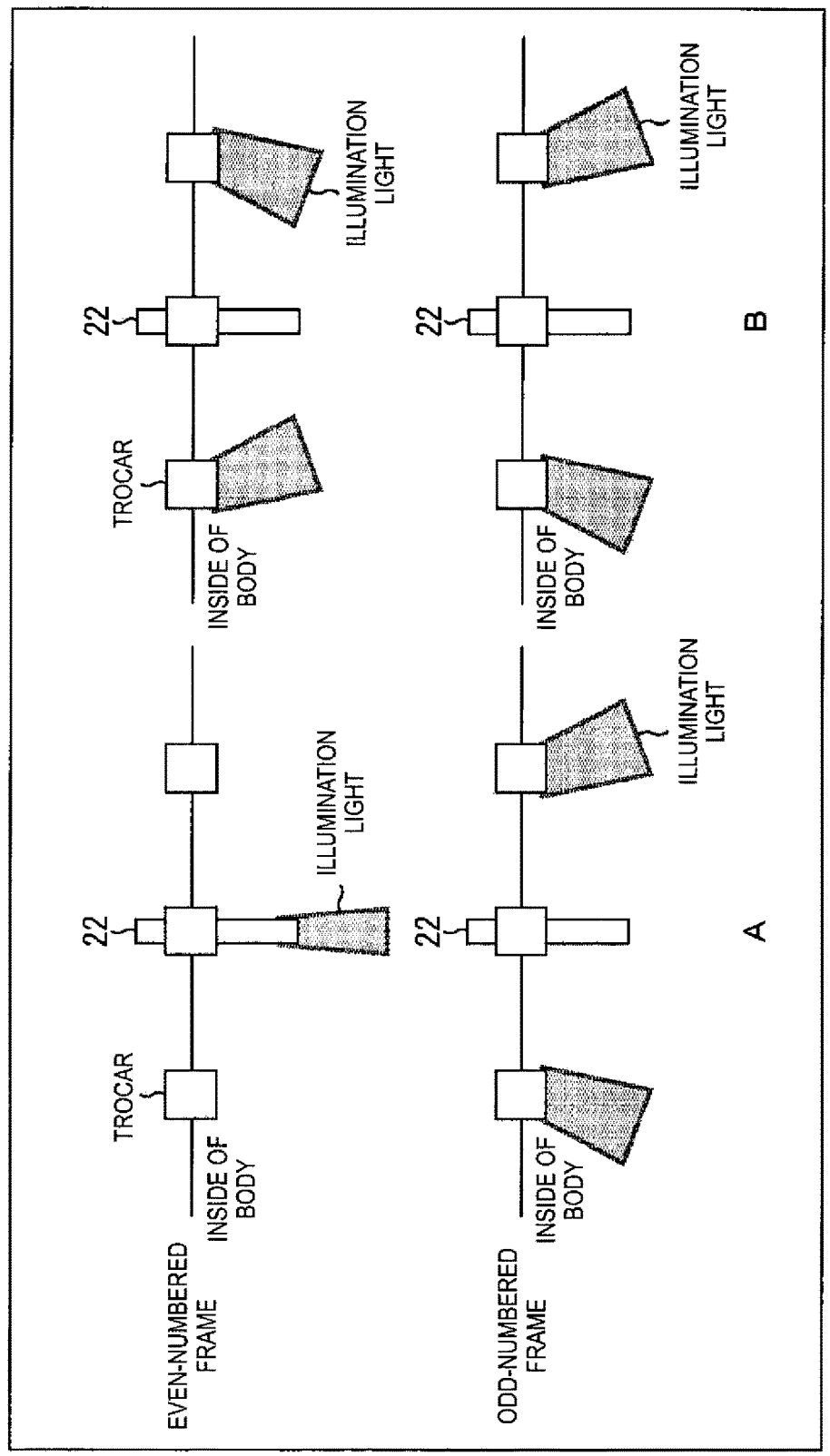

[Fig. 14]
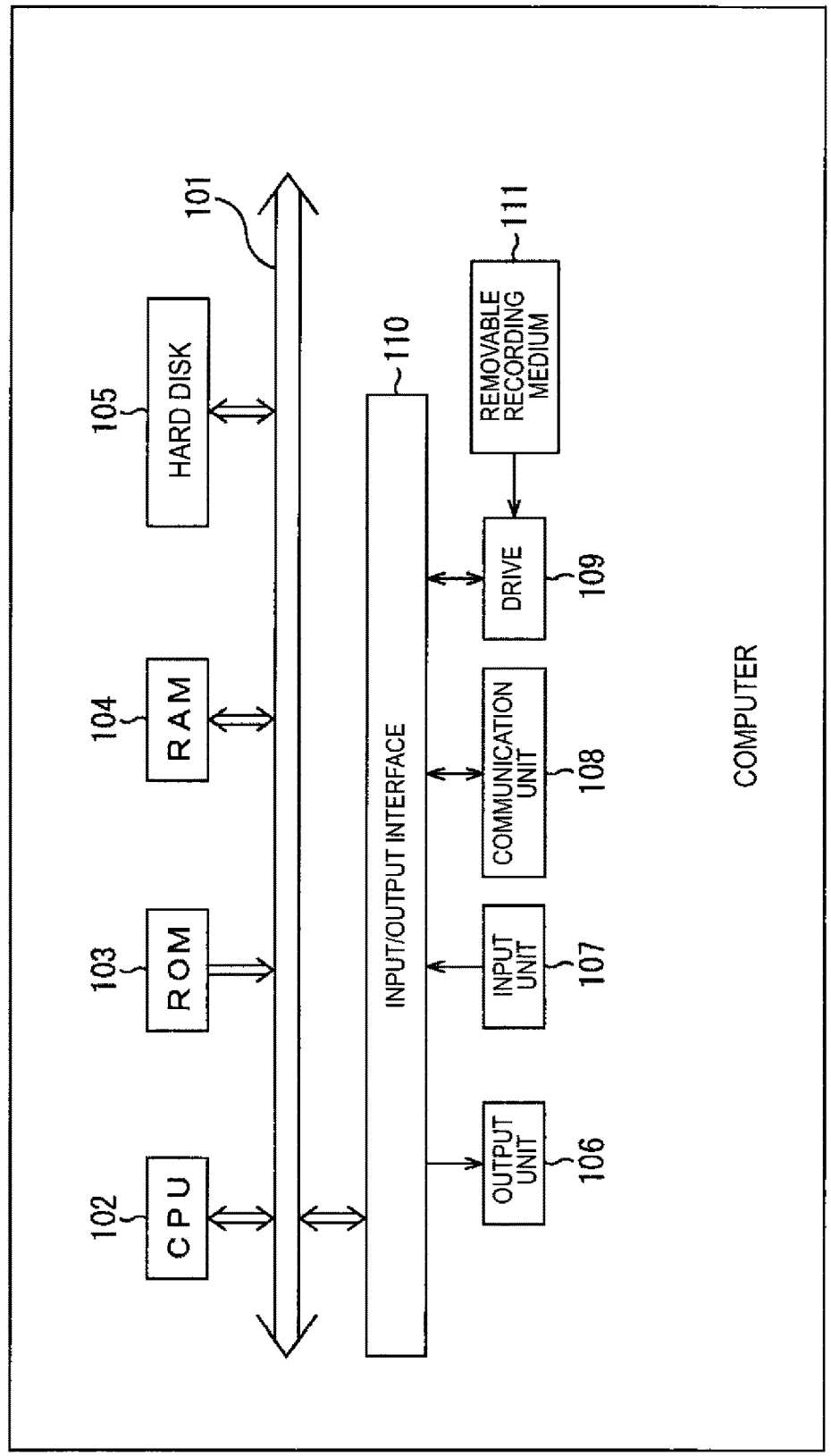

ENDOSCOPIC SYSTEM, IMAGE PROCESSING APPARATUS, AND IMAGE PROCESSING METHOD

CROSS REFERENCE TO RELATED APPLICATIONS

This application claims the benefit of Japanese Priority Patent Application JP 2015-021078 filed Feb. 5, 2015, the entire contents of which are incorporated herein by reference.

TECHNICAL FIELD

The present technology relates to an image processing device, an image processing method, a program, and an endoscope system and particularly relates to, for example, an image processing device, an image processing method, a program, and an endoscope system, each of which is capable of suppressing specular reflection light components.

BACKGROUND ART

For example, in the case where a subject is observed with the use of an endoscope in a surgical operation or diagnosis, specular reflection (regular reflection) easily occurs. Specular reflection light caused by specular reflection prevents observation of the subject, and therefore some countermeasure against specular reflection is requested.

There are proposed, as technologies to deal with specular reflection, for example, a technology for estimating specular reflection light components corresponding to specular reflection light, which are included in an endoscope image obtained by photographing with the use of an endoscope, on the basis of a dichromatic reflection model and removing the specular reflection light components by image processing and a technology for adjusting brightness of an endoscope image (e.g., see PTLs 1 and 2).

CITATION LIST

Patent Literature

PTL 1: JP 2001-224549A
PTL 2: JP 2006-142003A

SUMMARY OF INVENTION

Technical Problem

Because specular reflection light components of an endoscope image prevent observation of unevenness, patterns, and the like of, for example, an organ serving as a subject, proposition of various technologies for suppressing specular reflection light components of an endoscope image is requested.

The present technology has been made in view of the circumstances and is capable of suppressing specular reflection light components.

Solution to Problem

An endoscopic system including an endoscope device configured to output image data, an illumination device configured to illuminate a body of a patient, and circuitry that obtains, from the image data, at least two frames each captured with a different illumination state, generates, from the at least two obtained frames, a composite image that has a reduced specular reflection light component with respect to at least one of the obtained frames, and generates a video signal including the composite image.

An image processing apparatus including processing circuitry that obtains, from the image data, at least two frames each captured with a different illumination state, generates, from the at least two obtained frames, a composite image that has a reduced specular reflection light component with respect to at least one of the obtained frames, and generates a video signal including the composite image.

An image processing method for processing image data obtained from an endoscope device configured to output the image data, including obtaining, from the image data, at least two frames each captured with a different illumination state, generating, from the at least two obtained frames, a composite image that has a reduced specular reflection light component with respect to at least one of the obtained frames, and generating a video signal including the composite image.

Advantageous Effects of Invention

According to an embodiment of the present technology, it is possible to suppress specular reflection light components.

Note that the effect described herein is not necessarily limited and may be any one of effects described in the present disclosure.

BRIEF DESCRIPTION OF DRAWINGS

FIG. 1 is a block diagram showing a configuration example of an embodiment of an endoscope system to which the present technology is applied.

FIG. 2 illustrates a use example of an endoscope system.

FIG. 3 illustrates an example of an illumination method of illuminating a subject in an endoscope system.

FIG. 4 illustrates an example of adjustment of an illumination direction in an illumination unit 17.

FIG. 5 illustrates outlines of composition processing performed in a signal processing unit 13.

FIG. 6 shows examples of amounts of exposure and gains in a central irradiation image and a peripheral irradiation image.

FIG. 7 shows examples of setting of weight a.

FIG. 8 illustrates an example of timings of composition processing performed in the signal processing unit 13.

FIG. 9 illustrates another example of the timings of the composition processing performed in the signal processing unit 13.

FIG. 10 is a flowchart showing an example of processing of an endoscope system.

FIG. 11 is a flowchart showing an example of composition processing.

FIG. 12 illustrates other examples of the illumination method of illuminating a subject in an endoscope system.

FIG. 13 illustrates still another example of the illumination method of illuminating a subject in an endoscope system.

FIG. 14 is a block diagram showing a configuration example of an embodiment of a computer to which the present technology is applied.

DESCRIPTION OF EMBODIMENTS

<Embodiment of Endoscope System to which Present Technology is Applied>

FIG. 1 is a block diagram showing a configuration example of an embodiment of an endoscope system to which the present technology is applied.

In FIG. 1, the endoscope system includes an endoscope 11, a memory 12, a signal processing unit 13, a display unit 14, a photographing control unit 15, an illumination control unit 16, and an illumination unit 17.

The endoscope 11 includes, for example, an image sensor 11A such as a charge coupled device (CCD) or a complementary metal oxide semiconductor (CMOS) sensor and supplies a photograph image obtained by photographing a subject with the use of the image sensor 11A to the memory 12 and the signal processing unit 13.

Herein, the endoscope system of FIG. 1 is, for example, a medical endoscope system, and a living body serving as a subject, that is, for example, tissue of a body cavity of a patient is photographed in the image sensor 11A of the endoscope 11. Then, an endoscope image, which is a living body image obtained by photographing the living body, is supplied to the memory 12 and the signal processing unit 13 from the endoscope 11.

Note that, although not illustrated, the endoscope 11 includes, for example, an optical system such as a focus lens and a stop as necessary.

Further, the endoscope 11 can photograph the subject to produce, as an endoscope image, a two-dimensional (2D) image and a 3D image.

The memory 12 temporarily stores the endoscope image supplied from (the image sensor 11A of) the endoscope 11.

The signal processing unit 13 performs signal processing with the use of the endoscope image supplied from (the image sensor 11A of) the endoscope 11 or the endoscope image stored in the memory 12 and supplies an image obtained as a result of the signal processing to the display unit 14.

Herein, the signal processing performed in the signal processing unit 13 is, for example, demosaicing (developing) for obtaining values of RGB of each pixel in an image in a Bayer array and composition processing described below. In the composition processing, the endoscope image from the endoscope 11 and the endoscope image stored in the memory 12 are composed and a composite image obtained as a result of the composition processing is supplied to the display unit 14.

The display unit 14 displays the composite image supplied from the signal processing unit 13. The display unit 14 can be, for example, a display integrated with the signal processing unit 13, a stationary display separated from the signal processing unit 13, or a head mounted display.

The photographing control unit 15 controls photographing of the endoscope image in (the image sensor 11A of) the endoscope 11. Further, the photographing control unit 15 performs control to supply the endoscope image obtained by photographing in the endoscope 11 to the memory 12 or the signal processing unit 13.

Further, the photographing control unit 15 sets a condition of illumination (illumination condition) suitable for a frame of the endoscope image obtained by photographing in the endoscope 11 and supplies the condition to the illumination control unit 16.

That is, the endoscope image is obtained by photographing at a predetermined frame rate in the endoscope 11. The photographing control unit 15 sets an illumination condition for each frame of the endoscope image and supplies the illumination condition to the illumination control unit 16.

The illumination control unit 16 controls the illumination unit 17 so that a subject is illuminated in accordance with the illumination condition from the photographing control unit 15.

The illumination unit 17 illuminates the subject by emitting illumination light in accordance with control of the illumination control unit 16.

Herein, the illumination unit 17 includes all mechanisms for irradiating a subject with illumination light, such as a light source including a halogen lamp, a xenon lamp, a light emitting diode (LED), or the like, which emits light as illumination light, and an optical component including a light guide cable for guiding the illumination light emitted from the light source to the subject.

The illumination unit 17 irradiates the subject with illumination light in different illumination directions in, for example, an even-numbered frame and an odd-numbered frame in accordance with control of the illumination control unit 16.

That is, in the case where an endoscope image of the even-numbered frame is obtained by photographing, the illumination unit 17 irradiates the subject with, for example, illumination light in an illumination direction (first illumination direction) (hereinafter, also referred to as a central direction) toward a central part of the subject projected on the endoscope image.

Meanwhile, in the case where an endoscope image of the odd-numbered frame is obtained by photographing, the illumination unit 17 irradiates the subject with, for example, illumination light in an illumination direction (second illumination direction) (hereinafter, also referred to as a peripheral direction) toward a peripheral part of the subject projected on the endoscope image.

As a result, in the endoscope 11, an image obtained by photographing the subject irradiated with illumination light in the central direction can be obtained as the endoscope image of the even-numbered frame (first photograph image), and an image obtained by photographing the subject irradiated with illumination light in the peripheral direction can be obtained as the endoscope image of the odd-numbered frame (second photograph image).

In the composition processing performed in the signal processing unit 13, the endoscope image of the even-numbered frame and the endoscope image of the odd-numbered frame described above are composed.

Note that a part or all of the illumination unit 17 can be included in the endoscope 11.

The number of illumination light beams emitted from the illumination unit 17 is not particularly limited. That is, the illumination unit 17 can emit a single or a plurality of illumination light beams.

The subject can be irradiated with illumination light in the central direction in the case where the endoscope image of the odd-numbered frame is obtained by photographing, instead of the even-numbered frame, whereas the subject can be irradiated with illumination light in the peripheral direction in the case where photographing the endoscope image of the even-numbered frame is obtained by photographing, instead of the odd-numbered frame.

The number of illumination directions of illumination light can be not only two directions, i.e., the central direction and the peripheral direction, but also three or more directions.

That is, the number of illumination directions of illumination light can be, for example, three directions, i.e., a direction toward a left side of the subject, a direction toward the center of the subject, and a direction toward a right side of the subject, or four directions, i.e., directions toward an upper left side, a lower left side, an upper right side, and a lower right side of the subject.

In the case where the number of illumination directions of illumination light are K directions, for example, images of K frames whose illumination directions are the K illumination directions, respectively, are obtained by photographing in the endoscope system as endoscope images of the consecutive K frames, and the endoscope images of the consecutive K frames are composed as a composite image of a single frame.

FIG. 2 illustrates a use example of the endoscope system of FIG. 1.

The endoscope system of FIG. 1 is used for, for example, endoscopic operation in which a surgical part 32, which is a part in a body to be subjected to a surgical operation, is photographed as a subject and an endoscope image (composite image) on which the subject is projected is displayed on the display unit 14, and a doctor performs an operation on the surgical part 32 while watching the endoscope image.

The endoscope 11 is inserted into, for example, a body cavity of a patient (human body), and an endoscope image of tissue in the body cavity serving as a subject is obtained by photographing.

That is, the endoscope 11 includes, from its appearance, for example, a camera head 21 that an operator (doctor) who performs a surgical operation as a user of the endoscope system operates by his/her hand and a slender and tubular endoscope scope 22 to be inserted into a body of a patient.

In endoscopic operation, the endoscope scope 22 of the endoscope 11 and pairs of forceps 31 which are treatment tools are inserted into a body of a patient as illustrated in, for example, FIG. 2.

In the endoscope 11, for example, illumination light emitted by the illumination unit 17 is emitted through a tip end of the endoscope scope 22, the surgical part 32 serving as a subject in the body of the patient is illuminated with the illumination light. Further, in the endoscope 11, reflected light obtained by reflecting the illumination light in the surgical part 32 enters the tip end of the endoscope scope 22 and is received by the image sensor 11A of the endoscope 11. Thus, the surgical part 32 serving as a subject is photographed.

Note that, in the endoscope 11, the image sensor 11A can be provided in, for example, the camera head 21 or the tip end part of the endoscope scope 22. In the case where the image sensor 11A is provided in the camera head 21 of the endoscope 11, an optical component that leads reflected light, which is emitted from the subject (surgical part 32) and enters the tip end of the endoscope scope 22, to the image sensor 11A of the camera head 21 is provided in the endoscope scope 22.

Herein, in a general endoscope, a light guide for guiding illumination light emitted by a light source substantially overlaps an optical axis of (the image sensor included in) the endoscope because of its structure as disclosed in, for example, JP H11-104075A and JP 2011-120646A. Further, in order that a doctor performs a surgical operation and diagnosis, the tip end of the endoscope scope is approached to a surgical part serving as a subject and the surgical part is illuminated at a close distance.

Therefore, specular reflection light, which is caused by specular reflection of illumination light, easily occurs in the surgical part serving as a subject.

Specular reflection light components corresponding to specular reflection light, which are in an endoscope image obtained by photographing a subject with the use of the endoscope, conceal unevenness and patterns that originally exist on a surface of a subject. This prevents a doctor from observing a surgical part in some cases.

Methods of suppressing specular reflection light components are, for example, a method of estimating specular reflection light components on the basis of a dichromatic reflection model and removing the specular reflection light components by image processing and a method of adjusting a brightness signal, as disclosed in PTLs 1 and 2.

However, in the method disclosed in PTL 1, specular reflection light components are estimated by using an object in chromatic color as a target and cannot be estimated by using an object in color other than chromatic color as a target. Further, in the case where a sensor for use in photographing is saturated in estimation of specular reflection light components by using an object in chromatic color as a target, specular reflection light components cannot be correctly estimated because of lack of information on chroma. Therefore, it is necessary to take a photograph so as not to exceed sensitivity of the sensor.

Further, in the method disclosed in PTL 2, a high-brightness tone is compressed, and therefore contrast of the image is reduced, which may result in preventing observation of a subject and losing original texture of an organ.

In view of this, in the endoscope system of FIG. 1, an endoscope image is obtained by photographing a subject while irradiating the subject with illumination light in the central direction in order to obtain an endoscope image of an even-numbered frame and irradiating the subject with illumination light in the peripheral direction in order to obtain an endoscope image of an odd-numbered frame.

Then, in the endoscope system of FIG. 1, the endoscope image of the even-numbered frame, which is obtained by photographing the subject irradiated with illumination light in the central direction, and the endoscope image of the odd-numbered frame, which is obtained by photographing the subject irradiated with illumination light in the peripheral direction, are composed to generate a composite image in which specular reflection light components are suppressed.

<Example of Illumination Method>

FIG. 3 illustrates an example of an illumination method of illuminating a subject in the endoscope system in FIG. 1.

FIG. 3A is a front view illustrating a configuration example of the tip end of the endoscope scope 22 constituting the endoscope 11, assuming that the tip end is the front.

FIG. 3B is side views illustrating a configuration example of the tip end of the endoscope scope 22.

In FIG. 3A, a photographing window and illumination windows are provided in the tip end of the endoscope scope 22.

Reflected light from a subject enters the photographing window and is led to the image sensor 11A.

Note that, in FIG. 3, the front of the tip end of the endoscope scope 22 has a (substantially) circular shape, and the photographing window is provided in a central part of the circle.

The illumination windows are part of the illumination unit 17, and illumination light is emitted from the illumination windows.

Note that, in FIG. 3, four illumination windows are provided around the photographing window. However, the number of illumination windows are not limited to four. That is, one, two, three, or five or more illumination windows can be provided in the endoscope scope 22.

Illumination light is emitted through the illumination windows constituting the illumination unit 17 in accordance with control of the illumination control unit 16.

In FIG. 3, an illumination direction of illumination light is switched to the central direction or the peripheral direction so that, in the case where an endoscope image of an even-numbered frame is obtained by photographing, illumination light whose illumination direction is the central direction is emitted through the illumination windows, and, in the case where an endoscope image of an odd-numbered frame is obtained by photographing, illumination light whose illumination direction is the peripheral direction is emitted.

As a result, in the endoscope 11, an image on which a subject irradiated with illumination light in the central direction is projected is obtained by photographing as the endoscope image of the even-numbered frame, and an image on which the subject irradiated with illumination light in the peripheral direction is projected is obtained by photographing as the endoscope image of the odd-numbered frame.

In the illumination unit 17, for example, an illumination direction of illumination light with which a subject is illuminated can be mechanically controlled for each frame or can be adjusted (changed) with the use of optical components such as a mirror and a condensing lens.

FIG. 4 illustrates an example of adjustment of an illumination direction in the illumination unit 17.

In FIG. 4, in the illumination unit 17, illumination light emitted from the light source (not illustrated) passes through the light guide cable provided in the endoscope scope 22, reaches the illumination window provided in the tip end of the endoscope scope 22, and is emitted through the illumination windows.

In FIG. 4, the illumination window rotates (swings) around a rotation axis which is a direction vertical to a radius of the front circle of the tip end of the endoscope scope 22. By rotating the illumination window, an illumination direction of illumination light is adjusted to the central direction or the peripheral direction as in, for example, a flexible scope.

In FIG. 4, illumination light is constantly emitted, and the illumination direction is adjusted for each frame by rotating the illumination window. With this, in the case where an endoscope image of an even-numbered frame is obtained by photographing, illumination light whose illumination direction is the central direction is emitted from the illumination window, whereas, in the case where an endoscope image of an odd-numbered frame is obtained by photographing, illumination light whose illumination direction is the peripheral direction is emitted therefrom.

<Composition Processing>

FIG. 5 illustrates outlines of composition processing performed in the signal processing unit 13 of FIG. 1.

In the composition processing, an endoscope image of an even-numbered frame and an endoscope image of an odd-numbered frame are composed.

As described above, in the case where the endoscope image of the even-numbered frame is obtained by photographing, illumination light in the central direction is emitted, whereas, in the case where the endoscope image of the odd-numbered frame is obtained by photographing, illumination light in the peripheral direction is emitted.

As a result, in the even-numbered frame, illumination light is concentrated in a central part of the endoscope image, whereas, in the odd-numbered frame, illumination light is dispersed in a peripheral part of the endoscope image.

Therefore, in the endoscope image of the even-numbered frame, a region A-1 in the central part is bright and a region A-2 in the peripheral part is darker than the region A-1 in the central part. Meanwhile, in the endoscope image of the odd-numbered frame, a region B-2 in the peripheral part is bright and a region B-1 in the central part is darker than the region B-2 in the peripheral part.

As to the region A-1 in the central part of the endoscope image of the even-numbered frame, optical axes of illumination light are close to an optical axis of the image sensor 11A, and therefore specular reflection light components are easily included.

Meanwhile, as to the region A-2 in the peripheral part of the endoscope image of the even-numbered frame and the region B-1 in the central part of the endoscope image of the odd-numbered frame and the region B-2 in the peripheral part (the whole region in the endoscope image of the odd-numbered frame), shift between the optical axes of illumination light and the optical axis of the image sensor 11A is large. Therefore, specular reflection light components are not easily included therein.

In the composition processing, a composite image in which specular reflection light components are suppressed (having no specular reflection light component) is generated by appropriately composing the endoscope image of the even-numbered frame and the endoscope image of the odd-numbered frame described above.

Further, the endoscope image of the even-numbered frame and the endoscope image of the odd-numbered frame are photograph images having different light exposure conditions, and therefore composition of the endoscope image of the even-numbered frame and the endoscope image of the odd-numbered frame can bring about a high dynamic range (HDR) effect.

That is, a composite image having a high dynamic range can be generated by the composition processing of the endoscope image of the even-numbered frame and the endoscope image of the odd-numbered frame.

Hereinafter, an endoscope image of an even-numbered frame, which is obtained by photographing a subject while irradiating the subject with illumination light in the central direction, will be also referred to as a central irradiation image. Further, hereinafter, an endoscope image of an odd-numbered frame, which is obtained by photographing a subject while irradiating the subject with illumination light in the peripheral direction, will be also referred to as a peripheral irradiation image.

FIG. 6 shows examples of amounts of exposure and gains in a central irradiation image and a peripheral irradiation image.

FIG. 6A shows an example of (distribution of) amounts of exposure of the central irradiation image and the peripheral irradiation image.

In FIG. 6A, a horizontal axis indicates positions (coordinates) of the central irradiation image and the peripheral irradiation image in a horizontal direction or a vertical direction, and a vertical axis indicates amounts of exposure (brightness).

The central irradiation image is an image obtained by photographing a subject while irradiating the subject with illumination light in an illumination direction toward a central part of the central irradiation image, and therefore an amount of exposure of the central part is large and an amount of exposure of a peripheral part is small.

Meanwhile, the peripheral irradiation image is an image obtained by photographing the subject while irradiating the subject with illumination light in an illumination direction toward the peripheral part of the peripheral irradiation image, and therefore an amount of exposure of the central part is small and an amount of exposure of the peripheral part is large.

Note that the amount of exposure of the central irradiation image can be measured by an arbitrary method.

Further, the amount of exposure of the central irradiation image can be obtained in advance by, for example, simulation, i.e., by photographing the subject while irradiating the subject with illumination light in the central direction.

In the case where the amount of exposure of the central irradiation image is obtained in advance by, for example, simulation, (distribution of) an amount of exposure is obtained in advance, or, for example, amounts of exposure corresponding to distances between the subject and the endoscope scope 22 can be obtained in advance.

In the case where the amounts of exposure corresponding to the distances between the subject and the endoscope scope 22 are obtained in advance, an actual distance between the subject and the endoscope scope 22 is measured when the endoscope system is used and an amount of exposure corresponding to the actual distance can be used as the amount of exposure of the central irradiation image.

The same applies to the amount of exposure of the peripheral irradiation image.

The amount of exposure of the central irradiation image and the amount of exposure of the peripheral irradiation image are different depending on a position (pixel). Therefore, in the case where the central irradiation image and the peripheral irradiation image are composed, the signal processing unit 13 multiplies, for example, an appropriate gain by each pixel of the central irradiation image and each pixel of the peripheral irradiation image in order to make the amounts of exposure uniform.

That is, the signal processing unit 13 detects, for example, the largest amount of exposure among amounts of exposure of the central irradiation image and multiplies each pixel of the central irradiation image and each pixel of the peripheral irradiation image by a gain corresponding to an amount of exposure of the pixel on the basis of the largest amount of exposure.

Specifically, the signal processing unit 13 sets a gain of a pixel having the largest amount of exposure of the central irradiation image to 1.0. Then, based on the gain of the pixel having the largest amount of exposure of the central irradiation image, the signal processing unit 13 sets, in each pixel of the central irradiation image and each pixel of the peripheral irradiation image, a gain having a value that is in inverse proportion to an amount of exposure of the pixel.

FIG. 6B shows an example of (distribution of) gains that are set in the central irradiation image and the peripheral irradiation image.

In FIG. 6B, a horizontal axis indicates positions of the central irradiation image and the peripheral irradiation image in a horizontal direction or a vertical direction and a vertical axis indicates gains that are set in the signal processing unit 13.

In FIG. 6B, a gain of each pixel of the central irradiation image and a gain of each pixel of the peripheral irradiation image have values that are in inverse proportion to amounts of exposure of the pixels.

The signal processing unit 13 multiplies gains by the central irradiation image and the peripheral irradiation image, and the central irradiation image and the peripheral irradiation image to which the gains have been multiplied are composed.

That is, herein, pixel values in attention positions observed in the central irradiation image and the peripheral irradiation image are denoted by Pc and Po. Further, gains of pixels (gains that are set in pixels) in the attention positions of the central irradiation image and the peripheral irradiation image are denoted by Gc and Go.

In this case, pixel values Vc and Vo of pixels in the attention positions of the central irradiation image and the peripheral irradiation image to which the gains have been multiplied are represented by a formula $Vc=Pc*Gc$ and a formula $Vo=Po*Go$, respectively.

For example, the signal processing unit 13 obtains, as a pixel value C of a pixel in an attention position of a composite image, a weighting addition value of the pixel values Vc and Vo of the pixels in the attention positions of the central irradiation images and the peripheral irradiation images to which the gains have been multiplied.

That is, herein, assuming that weight used for obtaining the weighting addition value of the pixel values Vc and Vo is denoted by a, for example, the signal processing unit 13 obtains the pixel value C of the pixel in the attention position of the composite image in accordance with a formula $C=a*Vc+(1-a)*Vo$.

However, for example, the signal processing unit 13 sets, as the weight a, a value falling within a range represented by a formula $0.0=<a=<1.0$ on the basis of the pixel value Vc or Vo of the pixel in the attention position of the central irradiation image or the peripheral irradiation image (to which the gains have been multiplied).

FIG. 7 shows examples of setting of the weight a.

In FIG. 7, a horizontal axis indicates the pixel value Vc or Vo of the pixel in the attention position of the central irradiation image or peripheral irradiation image, and a vertical axis indicates the weight a.

In the case where the amount of exposure of the pixel in the attention position of the central irradiation image is larger than the amount of exposure of the pixel in the attention position of the peripheral irradiation image, the weight a is set in accordance with the pixel value Vc of the pixel in the attention position of the central irradiation image, as shown in FIG. 7A.

Meanwhile, in the case where the amount of exposure of the pixel in the attention position of the central irradiation image is not larger than the amount of exposure of the pixel in the attention position of the peripheral irradiation image, the weight a is set in accordance with the pixel value Vo of the pixel in the attention position of the peripheral irradiation image, as shown in FIG. 7B.

Herein, in FIG. 7A, the weight a has such a property that is reduced from 1.0 with respect to increase in the pixel value Vc of the pixel in the attention position of the central irradiation image. The reduction herein means that a reduction amount is 0 or more.

Further, in FIG. 7B, the weight a has such a property that is increased from 0.0 with respect to increase in the pixel value Vo of the pixel in the attention position of the peripheral irradiation image. The increase herein means that an increase amount is 0 or more.

In FIG. 7A, in the case where the pixel value Vc of the pixel in the attention position of the central irradiation image is smaller (or is equal to or smaller) than a threshold TH, the weight a is set to 1. Further, in FIG. 7A, in the case where the pixel value Vc of the pixel in the attention position of the central irradiation image is equal to or larger (or is larger) than the threshold TH, the weight a is set to 0.

In FIG. 7B, in the case where the pixel value Vo of the pixel in the attention position of the peripheral irradiation image is smaller than the threshold TH, the weight a is set to 0. Further, in FIG. 7B, in the case where the pixel value Vo of the pixel in the attention position of the peripheral irradiation image is equal to or larger than the threshold TH, the weight a is set to 1.

The threshold TH can be, for example, the smallest pixel value of a pixel which is highly likely to include specular reflection light components. The threshold TH can be estimated by, for example, simulation.

In the case where 0 or 1 is set as the weight a as described above, in the composition processing performed in accordance with a formula C=a*Vc+(1−a)*Vo, one of the pixel values Vc and Vo of the pixels in the attention positions of the central irradiation image and the peripheral irradiation image practically serves as a pixel value in an attention position of a composite image.

That is, in the case where the amount of exposure of the pixel in the attention position of the central irradiation image is larger than the amount of exposure of the pixel in the attention position of the peripheral irradiation image (FIG. 7A) and the pixel value Vc of the pixel in the attention position of the central irradiation image is smaller than the threshold TH, the weight a is 1, and the pixel value Vc of the pixel in the attention position of the central irradiation image is obtained as the pixel value C of the pixel in the attention position of the composite image. Further, in the case where the pixel value Vc of the pixel in the attention position of the central irradiation image is not smaller than the threshold TH, the weight a is 0, and the pixel value Vo of the pixel in the attention position of the peripheral irradiation image is obtained as the pixel value C of the pixel in the attention position of the composite image.

Meanwhile, in the case where the amount of exposure of the pixel in the attention position of the central irradiation image is not larger than the amount of exposure of the pixel in the attention position of the peripheral irradiation image (FIG. 7B) and the pixel value Vo of the pixel in the attention position of the peripheral irradiation image is smaller than the threshold TH, the weight a is 0, and the pixel value Vo of the pixel in the attention position of the peripheral irradiation image is obtained as the pixel value C of the pixel in the attention position of the composite image. Further, in the case where the pixel value Vo of the pixel in the attention position of the peripheral irradiation image is not smaller than the threshold TH, the weight a is 1, and the pixel value Vc of the pixel in the attention position of the central irradiation image is obtained as the pixel value C of the pixel in the attention position of the composite image.

Herein, in the case where the attention positions are central parts of the endoscope images (central irradiation image and peripheral irradiation image), the amount of exposure of the pixel in the attention position of the central irradiation image is larger than the amount of exposure of the pixel in the attention position of the peripheral irradiation image. In this case, in the case where the pixel value Vc of the pixel in the attention position of the central irradiation image is smaller than the threshold TH, it is estimated that the pixel value Vc of the pixel in the attention position of the central irradiation image includes no specular reflection light component, and the pixel value Vc serves as the pixel value C of the pixel in the attention position of the composite image as it is.

Further, in the case where the pixel value Vc of the pixel in the attention position of the central irradiation image is not smaller than the threshold TH, it is estimated that the pixel value Vc of the pixel in the attention position of the central irradiation image may include specular reflection light components, and the pixel value Vo of the pixel in the attention position of the peripheral irradiation image serves as the pixel value C of the pixel in the attention position of the composite image.

Meanwhile, in the case where the attention positions are peripheral parts, the amount of exposure of the pixel in the attention position of the peripheral irradiation image is larger than the amount of exposure of the pixel in the attention position of the central irradiation image. In this case, in the case where the pixel value Vo of the pixel in the attention position of the peripheral irradiation image is smaller than the threshold TH, it is estimated that the pixel value Vo of the pixel in the attention position of the peripheral irradiation image includes no specular reflection light component, and the pixel value Vo serves as the pixel value C of the pixel in the attention position of the composite image as it is.

Further, in the case where the pixel value Vo of the pixel in the attention position of the peripheral irradiation image is not smaller than the threshold TH, it is estimated that the pixel value Vo of the pixel in the attention position of the peripheral irradiation image may include specular reflection light components, and the pixel value Vc of the pixel in the attention position of the central irradiation image serves as the pixel value C of the pixel in the attention position of the composite image.

Specular reflection easily occurs in a subject projected on a central part of an endoscope image in the case where an amount of exposure is large, and therefore, in the case where a pixel value Vc (Pc) of a pixel in the central part of the central irradiation image is a saturation value or a value extremely close to the saturation value, there is a high possibility that specular reflection light components are included in the pixel value Vc.

Therefore, as described above, in the case where the amount of exposure of the pixel in the attention position of the central irradiation image is larger (than the amount of exposure of the pixel in the attention position of the peripheral irradiation image) and the pixel value Vc of the pixel in the attention position of the central irradiation image is not smaller than the threshold TH, it is estimated, in the signal processing unit 13, that the pixel value Vc of the pixel in the attention position of the central irradiation image may include specular reflection light components, and the pixel value Vo of the pixel in the attention position of the peripheral irradiation image serves as the pixel value C of the pixel in the attention position of the composite image. Therefore, it is possible to obtain a composite image in which specular reflection light components are suppressed, i.e. a composite image in which no specular reflection light component is detected in an endoscope image.

Note that, in FIG. 7, in the case where the amount of exposure of the pixel in the attention position of the central irradiation image is larger than the amount of exposure of the pixel in the attention position of the peripheral irradiation image and the pixel value Vc of the pixel in the attention position of the central irradiation image is not smaller than the threshold TH, it is estimated that the pixel value Vc may include specular reflection light components, and the pixel value Vo of the pixel in the attention position of the peripheral irradiation image is obtained as the pixel value C of the pixel in the attention position of the composite image.

Further, in the case where the amount of exposure of the pixel in the attention position of the central irradiation image is not larger than the amount of exposure of the pixel in the attention position of the peripheral irradiation image and the pixel value Vo of the pixel in the attention position of the peripheral irradiation image is not smaller than the threshold TH, it is estimated that the pixel value Vo may include specular reflection light components, and the pixel value Vc of the pixel in the attention position of the central irradiation image is obtained as the pixel value C of the pixel in the attention position of the composite image.

However, even in the case where the amount of exposure of the pixel in the attention position of the central irradiation image is larger than the amount of exposure of the pixel in the attention position of the peripheral irradiation image and the pixel value Vc of the pixel in the attention position of the central irradiation image is smaller than the threshold TH, there is a possibility that the pixel value Vc includes specular reflection light components.

Similarly, even in the case where the amount of exposure of the pixel in the attention position of the central irradiation image is not larger than the amount of exposure of the pixel in the attention position of the peripheral irradiation image and the pixel value Vo of the pixel in the attention position of the peripheral irradiation image is smaller than the threshold TH, there is a possibility that the pixel value Vo includes specular reflection light components.

In view of this, the signal processing unit 13 can perform, with respect to the pixels in the attention positions of the central irradiation image and the peripheral irradiation image, processing for detecting specular reflection light components, that is, for example, processing for detecting specular reflection light components with the use of a dichromatic reflection model or the like. Then, in the case where specular reflection light components are detected in one of the pixels in the attention positions of the central irradiation image and the peripheral irradiation image, a pixel value of the other one of the pixels can be employed as the pixel value C of the pixel in the attention position of the composite image instead of the weighting addition value obtained by using the weight a.

Although the weight a is set to 0 or 1 (is set to a value that is sharply changed from 0 or 1 to 1 or 0 in the threshold TH) in the above case, the weight a can be set to an arbitrary value falling within a range represented by a formula $0.0 \leq a \leq 1.0$ on the basis of the pixel value Vc or Vo of the pixel in the attention position of the central irradiation image or the peripheral irradiation image.

That is, in the case where, for example, the pixel value Vc or Vo is a value around the threshold TH, the weight a can be set to a value that is slowly changed from 1 to 0 or a value that is slowly changed from 0 to 1 in accordance with the pixel value Vc or Vo, as indicated by dotted lines of FIG. 7.

For example, for the pixel value Vc or Vo falling within a range of TH1 (<TH) to TH2 (>TH), the weight a can be set to a value that is slowly changed from 1 to 0 or a value that is slowly changed from 0 to 1 in accordance with the pixel value Vc or Vo, as indicated by the dotted lines of FIG. 7.

In this case, the pixel value C of the pixel in the attention position of the composite image is a value obtained by blending the pixel values Vc and Vo at a ratio corresponding to the weight a (a ratio corresponding to a difference between the pixel value Vc or Vo and the threshold TH).

It is possible to employ an arbitrary characteristic that the weight a is decreased from 1 with respect to increase in the pixel value Vc or an arbitrary characteristic that the weight a is increased from 0 with respect to increase in the pixel value Vo.

In the composition processing, an endoscope image of an even-numbered frame and an endoscope image of an odd-numbered frame are composed as described above, and, in the case where a composite image is generated, tones of the composite image are compressed.

That is, in the composition processing, gains are multiplied by the central irradiation image and the peripheral irradiation image, and the central irradiation image and the peripheral irradiation image to which the gains have been multiplied are composed. Therefore, the composite image is an image having a larger bit width than that of the central irradiation image or the peripheral irradiation image before the composition processing, i.e., an image having a high dynamic range.

For example, in the case where the largest value of a gain multiplied by the central irradiation image and the peripheral irradiation image is 16.0 ($=2^4$), a bit width of the composite image is larger by only 4 bits than a bit width of the central irradiation image or the peripheral irradiation image before the composition processing.

In the composition processing, the tones of the composite image are compressed so that, for example, the bit width of the composite image corresponds to the bit width of the central irradiation image or the peripheral irradiation image before the composition processing.

A method of compressing tones of a composite image can be, for example, a method of compressing tones with the use of a fixed tone curve or a method of switching a tone curve in accordance with a feature value of an image to compress tones. Further, a method of compressing tones of a composite image can be, for example, a method of performing division with the use of the largest value of a gain among gains multiplied by a central irradiation image and a peripheral irradiation image or other arbitrary methods.

FIG. 8 illustrates an example of timings of composition processing performed in the signal processing unit 13 of FIG. 1.

In FIG. 8, in the composition processing, an endoscope image (central irradiation image) of a certain even-numbered frame #2N and an endoscope image (peripheral irradiation image) of an odd-numbered frame #2N+1 subsequent to the even-numbered frame #2N are composed. Further, in the composition processing, thereafter, an endoscope image (central irradiation image) of an even-numbered frame #2N+2 subsequent to the odd-numbered frame #2N+1 and an endoscope image (peripheral irradiation image) of an odd-numbered frame #2N+3 subsequent to the even-numbered frame #2N+2 are composed.

In the composition processing of FIG. 8, the above composition of an endoscope image (central irradiation image) of an even-numbered frame and an endoscope image (peripheral irradiation image) of an odd-numbered frame is repeated.

In this case, a frame rate of a composite image obtained by composing an endoscope image of an even-numbered frame and an endoscope image of an odd-numbered frame is ½ of a frame rate of an endoscope image obtained by photographing in the endoscope 11.

Therefore, in the case where the composition processing is performed at the timings shown in FIG. 8, it is necessary to photograph an endoscope image at a frame rate that is twice as much as a frame rate demanded for the composite image in the endoscope 11.

FIG. 9 illustrates another example of the timings of the composition processing performed in the signal processing unit 13 of FIG. 1.

In FIG. 9, in the composition processing, an endoscope image (central irradiation image) of a certain even-numbered frame #2N and an endoscope image (peripheral irradiation image) of an odd-numbered frame #2N+1 subsequent to the even-numbered frame #2N are composed. Further, in the composition processing, thereafter, the endoscope image (peripheral irradiation image) of the odd-numbered frame #2N+1 that has been used for previous composition and an endoscope image (central irradiation image) of an even-numbered frame #2N+2 subsequent to the odd-numbered frame #2N+1 are composed.

In the composition processing of FIG. 9, the above composition of an endoscope image (central irradiation image) of an even-numbered frame and an endoscope image (peripheral irradiation image) of an odd-numbered frame is repeated.

In this case, a frame rate of a composite image obtained by composing an endoscope image of an even-numbered frame and an endoscope image of an odd-numbered frame is equal to a frame rate of an endoscope image obtained by photographing in the endoscope 11.

<Processing of Endoscope System>

FIG. 10 is a flowchart showing an example of processing of an endoscope system of FIG. 1.

Note that, in FIG. 10, for example, the composition processing is performed at the timings shown in FIG. 8.

In Step S11, control of illumination suitable for an attention frame to be obtained by photographing in the endoscope 11 is performed.

That is, in Step S11, the photographing control unit 15 sets an illumination condition suitable for the attention frame and supplies the illumination condition to the illumination control unit 16. The illumination control unit 16 controls the illumination unit 17 so as to illuminate a subject in accordance with the illumination condition from the photographing control unit 15.

The illumination unit 17 illuminates the subject by irradiating the subject with illumination light whose illumination direction is the central direction or the peripheral direction in accordance with control of the illumination control unit 16.

Thereafter, the processing proceeds from Step S11 to Step S12, and the endoscope 11 photographs the subject irradiated with illumination light by the illumination unit 17. With this, an endoscope image of the attention frame is acquired, and the processing proceeds to Step S13.

In Step S13, the photographing control unit 15 determines whether or not photographing of endoscope images necessary for composition of a composite image of a single frame has been completed in the endoscope 11.

In the case where it is determined that photographing of the endoscope images necessary for composition of the composite image of the single frame has not been completed in Step S13, the processing proceeds to Step S14.

In Step S14, the photographing control unit 15 supplies the endoscope image of the attention frame obtained by photographing in the endoscope 11 to the memory 12 from the endoscope 11 to write (store) the endoscope image. Then, the processing returns from Step S14 to Step S11, and the similar processing is repeated with respect to a frame subsequent to the current attention frame as a new attention frame.

In Step S13, in the case where it is determined that photographing of the endoscope images necessary for composition of the composite image of the single frame has been completed, the photographing control unit 15 supplies the endoscope image of the attention frame obtained by photographing in the endoscope 11 to the signal processing unit 13 from the endoscope 11.

Then, the processing proceeds from Step S13 to Step 15, and the signal processing unit 13 performs composition processing in which the endoscope image of the latest attention frame supplied from the endoscope 11 and an endoscope image of a frame immediately before the attention frame, the endoscope image being stored in the memory 12, are composed.

That is, assuming that the endoscope image of the attention frame is a peripheral irradiation image, a central irradiation image of a frame immediately before the peripheral irradiation image is currently stored in the memory 12, and, in the composition processing, the central irradiation image and the peripheral irradiation image are composed to generate a composite image.

The composite image obtained by the composition processing is supplied to the display unit 14 from the signal processing unit 13 and is displayed. Thus, the processing for displaying the composite image of the single frame is completed.

In order to display a composite image of the next frame, the processing is repeated in accordance with the flowchart of FIG. 10.

FIG. 11 is a flowchart showing an example of the composition processing performed in Step S15 of FIG. 10.

In Step S21, as described above with reference to FIG. 6, the signal processing unit 13 performs gain correction in which gains corresponding to amounts of exposure are multiplied by the central irradiation image and the peripheral irradiation image which are targets to undergo the composition processing, and the processing proceeds to Step S22.

In Step S22, as described above with reference to FIG. 7, the signal processing unit 13 sets the weight a on the basis of the pixel value Vc or Vo of the pixel in the central irradiation image or the peripheral irradiation image (to which the gains have been multiplied).

Further, as described above with reference to FIG. 7, the signal processing unit 13 composes the central irradiation image and the peripheral irradiation image with the use of the weight a to generate a composite image, and the processing proceeds from Step S22 to Step S23.

In Step S23, the signal processing unit 13 compresses tones of the composite image and supplies the composite image whose tones have been compressed to the display unit 14, and the composition processing is terminated (returns).

As described above, in the endoscope system of FIG. 1, a central irradiation image and a peripheral irradiation image, i.e., a plurality of endoscope images obtained by photographing a subject irradiated with illumination light in different illumination directions are composed to generate a composite image.

Therefore, it is possible to suppress specular reflection light components of a composite image, and a user who observes the composite image can satisfactorily recognize unevenness and patterns that originally exist on a surface of a subject projected on the composite image. It is also possible to obtain an image having a high dynamic range as the composite image.

<Another Example of Illumination Method>

FIG. 12 illustrates other examples of the illumination method of illuminating a subject in the endoscope system of FIG. 1.

That is, FIG. 12 is front views and side views showing configuration examples of the tip end of the endoscope scope 22 constituting the endoscope 11.

In FIG. 12, a photographing window and illumination windows are provided to the tip end of the endoscope scope 22 as in FIG. 3. However, in FIG. 12, the illumination windows are provided at least in a position closer to the center of a front circle of the tip end of the endoscope scope 22 (hereinafter, referred to as a position closer to the center of the scope) and in a position closer to a circumference (hereinafter, also referred to as a position closer to an outer circumference of the scope).

In FIG. 12A, a single illumination window is provided in a position closer to the center of the scope, and another illumination window is provided in a position closer to the outer circumference of the scope.

In FIG. 12B, a single toroidal illumination window is provided in a position closer to the center of the scope so as to surround a photographing window, and another toroidal illumination window is provided in a position closer to the outer circumference of the scope so as to surround the illumination window in the position closer to the center of the scope.

In FIG. 12C, four illumination windows are provided in positions closer to the center of the scope at intervals of an central angle of 90 degrees, and other four illumination windows are provided in positions closer to the outer circumference of the scope, the positions being outside the positions of the illumination windows closer to the center of the scope.

In FIG. 12D, four illumination windows are provided in positions closer to the center of the scope and other four illumination windows are provided in positions closer to the outer circumference of the scope as in FIG. 12C. However, in FIG. 12D, the four illumination windows in the positions closer to the outer circumference of the scope are provided to protrude to outside of the endoscope scope 22.

Note that, in FIG. 12D, the four illumination windows in the positions closer to the outer circumference of the scope can be received in the endoscope scope 22.

In the case where (the tip end of) the endoscope scope 22 is inserted into a body cavity, the four illumination windows in the positions closer to the outer circumference of the scope are received in the endoscope scope 22. Then, after the endoscope scope 22 is inserted into the body cavity, the illumination windows protrude to outside of the endoscope scope 22. Furthermore, in the case where the endoscope scope 22 is pulled out from the body cavity, the four illumination windows in the positions closer to the outer circumference of the scope are received in the endoscope scope 22 again.

In FIG. 12, illumination light in the central direction is emitted through the illumination windows in the positions closer to the center of the scope, and illumination light in the peripheral direction is emitted through the illumination windows in the positions closer to the outer circumference of the scope.

The illumination control unit 16 controls the illumination unit 17 so that, in the case where a central irradiation image, i.e., an endoscope image of an even-numbered frame is obtained by photographing, illumination light emitted through the illumination window in the position closer to the center of the scope is turned on and illumination light emitted through the illumination window in the position closer to the outer circumference of the scope is turned off.

Further, the illumination control unit 16 controls the illumination unit 17 so that, in the case where a peripheral irradiation image, i.e., an endoscope image of an odd-numbered frame is obtained by photographing, illumination light emitted through the illumination window in the position closer to the center of the scope is turned off and illumination light emitted through the illumination window in the position closer to the outer circumference of the scope is turned on.

It is possible to illuminate a subject with illumination light having different illumination directions by controlling illumination directions of illumination light as described above with reference to FIG. 3 and FIG. 4 or by switching on or off illumination light in the central direction, which is emitted through the illumination window in the position closer to the center of the scope, and illumination light in the peripheral direction, which is emitted through the illumination window in the position closer to the outer circumference of the scope, as described above with reference to FIG. 12.

Note that, in the case of FIG. 12D, the illumination windows in the positions closer to the outer circumference of the scope are distant from the position of the photographing window, as compared to the cases of FIG. 12A to FIG. 12C. Therefore, shift between an optical axis of illumination light and the optical axis of image sensor 11A is larger in the case of FIG. 12D. Therefore, the peripheral irradiation image includes specular reflection light components more rarely, as compared to the cases of FIG. 12A to FIG. 12C.

FIG. 13 illustrates still another example of the illumination method of illuminating a subject in the endoscope system of FIG. 1.

That is, FIG. 13 is cross-sectional views simply illustrating a state in which the endoscope 11 is inserted into the body cavity.

Although illumination light is emitted from the endoscope 11 in the above case, illumination light can be emitted from an external tool which is a tool that is different from the endoscope 11.

In FIG. 13, tubular trocars serving as external tools are provided in holes bored in a surface of a human body. In FIG. 13, for example, three trocars are linearly provided.

Further, in FIG. 13, among the three trocars, the endoscope scope 22 is inserted into a central trocar. Further, among the three trocars, two trocars at both ends are part of the illumination unit 17, and illumination windows (not illustrated) through which illumination light is emitted are provided in the two trocars.

In FIG. 13A, at least an illumination window in a position closer to the center of the scope, which has been described above with reference to FIG. 12, is provided in the endoscope scope 22, and illumination light in the central direction is emitted through the illumination window.

Further, in FIG. 13A, the two trocars at the both ends emit illumination light in the peripheral direction through the illumination windows provided in the trocars.

In FIG. 13A, in the case where a central irradiation image, i.e., an endoscope image of an even-numbered frame is obtained by photographing, the illumination control unit 16 controls the illumination unit 17 so as to turn on illumination light emitted through the illumination window of the endoscope scope 22 and turn off illumination light emitted through the illumination windows of the two trocars at the both ends.

In the case where a peripheral irradiation image, i.e., an endoscope image of an odd-numbered frame is obtained by photographing, the illumination control unit 16 controls the illumination unit 17 so as to turn off illumination light emitted through the illumination window of the endoscope scope 22 and turn on illumination light emitted through the illumination windows of the two trocars at the both ends.

As described above, illumination light in the central direction and illumination light in the peripheral direction are emitted from the endoscope scope 22 and the trocars in FIG. 13A, whereas illumination light in the central direction and illumination light in the peripheral direction are emitted only from the trocars in FIG. 13B.

That is, in FIG. 13B, in the case where the central irradiation image (endoscope image of even-numbered frame) is obtained by photographing, the illumination control unit 16 controls the illumination unit 17 so that illumination directions of illumination light emitted through the illumination windows of the two trocars at the both ends form the central direction.

Meanwhile, in the case where the peripheral irradiation image (endoscope image of odd-numbered frame) is obtained by photographing, the illumination control unit 16 controls the illumination unit 17 so that illumination directions of illumination light emitted through the illumination windows of the two trocars at the both ends form the peripheral direction.

As described above, in the case where illumination light is emitted from a trocar that is an external tool that is different from the endoscope 11, shift between an optical axis of the illumination light and an optical axis of the image sensor 11A is larger, as compared to the case where illumination light is emitted from the endoscope scope 22. Therefore, the peripheral irradiation image includes specular reflection light components more rarely.

Note that, as illustrated in FIG. 13B, in the case where illumination light is emitted only from the trocars and illumination light in the central direction emitted from the trocars does not have enough brightness to irradiate a subject, illumination light in the central direction can be emitted from the endoscope scope 22.

That is, in FIG. 13B, illumination light in the central direction can be also emitted from the endoscope 11 at a timing synchronized with a timing at which illumination light in the central direction is emitted through the illumination windows of the trocars.

Note that, although a trocar is employed as an external tool that emits illumination light in FIG. 13, the external tool that emits illumination light is not limited to the trocar. That is, as the external tool that emits illumination light, for example, a device only for illumination is employed, and the device only for illumination can be inserted into the trocar to illuminate a body cavity serving as a subject.

<Description of Computer to which Present Technology is Applied>

The above-mentioned series of processing of the signal processing unit 13 can be performed by hardware or software. In the case where the series of processing is performed by software, a program configuring the software is installed in a computer.

In view of this, FIG. 14 shows a configuration example of an embodiment of a computer to install a program for executing the above-mentioned series of processing.

The program can be stored in advance in a hard disk 105 or a ROM 103 serving as a recording medium included in the computer.

Alternatively, the program can be stored in a removable recording medium 111. The removable recording medium 111 can be provided as a so-called packaged software. Herein, examples of the removable recording medium 111 encompass a flexible disk, a compact disc read only memory (CD-ROM), a magneto optical (MO) disk, a digital versatile disc (DVD), a magnetic disk, and a semiconductor memory.

Note that the program can be installed in the computer from the removable recording medium 111 as described above or can be downloaded to the computer via a communication network or a broadcasting network to be installed in the hard disk 105 included therein. That is, for example, the program can be transferred to the computer from a download site via a satellite for digital satellite broadcasting in a wireless manner or can be transferred to the computer via a network such as a local area network (LAN) or the Internet in a wired manner.

The computer includes a central processing unit (CPU) 102, and an input/output interface 110 is connected to the CPU 102 via a bus 101.

In the case where a user inputs a command via the input/output interface 110 by, for example, operating an input unit 107, the CPU 102 executes the program stored in the read only memory (ROM) 103 in accordance with the command. Alternatively, the CPU 102 loads the program stored in the hard disk 105 into a random access memory (RAM) 104 and executes the program.

With this, the CPU 102 performs the processing in accordance with the above-mentioned flowchart or the processing by using the configuration of the above-mentioned block diagram. Then, for example, the CPU 102 outputs a result of the processing through an output unit 106 or transmits the result through a communication unit 108 via the input/output interface 110 as necessary and stores the result in the hard disk 105.

Note that the input unit 107 includes a keyboard, a mouse, a microphone, and/or the like. The output unit 106 includes a liquid crystal display (LCD), a speaker, and/or the like.

Herein, in this specification, the computer does not necessarily need to perform the processing in accordance with the program in order shown in the flowchart in a time series. That is, the processing performed by the computer in accordance with the program also includes processing executed in parallel or individually (for example, parallel processing or processing using objects).

Further, the program may be processed by a single computer (processor) or may be dispersedly processed by a plurality of computers. Further, the program may be transferred to and be executed by a remote computer.

Further, in this specification, a system means gathering of a plurality of constituent elements (device, module (component), and the like), and all the constituent elements may or may not be received in the same housing. Therefore, a plurality of devices received in different housings and connected via a network are a system, and a single device in which a plurality of modules are received in a single housing is also a system.

Note that embodiments of the present technology are not limited to the above embodiment, and various kinds of modification can be performed within the scope of the present technology.

For example, the present technology can employ a cloud computing configuration in which a single function is shared by a plurality of devices via a network and is cooperatively processed by the plurality of devices.

The above-mentioned steps shown in the flowcharts can be executed by a single device or can be cooperatively executed by a plurality of devices.

Further, in the case where a plurality of processes are included in a single step, the plurality of processes included in the single step can be executed by a single device or can be cooperatively executed by a plurality of devices.

The present technology is applicable to processing of an endoscope image obtained by photographing with the use of the endoscope 11 whose the endoscope scope 22 is inserted into a body, and, for example, processing of an endoscope image obtained by photographing with the use of a so-called capsule type endoscope.

Further, the present technology is applicable to processing of an image obtained by photographing (tissue of) a human body and processing of an image obtained by photographing a living body other than a human body.

Furthermore, the present technology is applicable to processing of an endoscope image (living body image) obtained by photographing a living body with the use of the endoscope 11 and, for example, processing of a living body image obtained by photographing a living body with the use of a video microscopy.

Still further, the present technology is applicable to processing of an endoscope image obtained by photographing a subject in a medical endoscope system and processing of an endoscope image obtained by photographing a subject other than a living body in an industrial endoscope system.

The effects described in this specification are merely examples and are not limited, and other effects may be exerted.

It should be understood by those skilled in the art that various modifications, combinations, sub-combinations and alterations may occur depending on design requirements and other factors insofar as they are within the scope of the appended claims or the equivalents thereof.

Additionally, the present technology may also be configured as below.

(1)
An endoscopic system including an endoscope device configured to output image data, an illumination device configured to illuminate a body of a patient, and circuitry configured to obtain, from the image data, at least two frames each captured with a different illumination state, generate, from the at least two obtained frames, a composite image that has a reduced specular reflection light component with respect to at least one of the obtained frames, and generate a video signal including the composite image.

(2)
The endoscopic system according to (1), wherein the endoscope device configured to output the image data at a first frame rate, and the video signal has a second frame rate that is lower than the first frame rate.

(3)
The endoscopic system according to (1), wherein the endoscope device configured to output the image data at a first frame rate, and the video signal has the first frame rate.

(4)
The endoscopic system according to (1), wherein the illumination device is configured to illuminate the body of the patient from different illumination positions to change the illumination state.

(5)
The endoscopic system according to (4), wherein the circuitry is further configured to instruct the illumination device to change the illumination positions.

(6)
The endoscopic system according to (1), wherein the circuitry is further configured to instruct the illumination device to change an illumination direction.

(7)
The endoscopic system according to (6), wherein the circuitry is further configured to instruct the illumination device to change the illumination direction in response to a frame being output by the endoscope device.

(8)
The endoscopic system according to (6), wherein the circuitry is further configured to instruct the illumination device to change the illumination direction in response to at least two frames being output by the endoscope device.

(9)
The endoscopic system according to (1), wherein the illumination direction is changed by a movement of the body of the patient.

(10)
The endoscopic system according to (1)-(9), further including a trocar configured to permit insertion of the illumination device in the body of the patient.

(11)
The endoscopic system according to (1)-(10), wherein the circuitry is further configured to perform image processing on the composite image generated from the combining of the at least two obtained frames.

(12)
An endoscope device, including processing circuitry configured to obtain, from the image data, at least two frames each captured with a different illumination state, generate, from the at least two obtained frames, a composite image that has a reduced specular reflection light component with respect to at least one of the obtained frames, and generate a video signal including the composite image.

(13)
The endoscope device according to (12), wherein the image data is output by an endoscope device at a first frame rate, and the video signal has a second frame rate that is lower than the first frame rate.

(14)
The endoscope device according to (12), wherein the image data is output by an endoscope device at a first frame rate at a first frame rate, and the video signal has the first frame rate.

(15)
The endoscope device according to (12), wherein the processing circuitry is further configured to instruct an illumination device to change an illumination position.

(16)
The endoscope device according to (15), wherein the processing circuitry is further configured to instruct the illumination device to change the illumination position in response to a frame being output by the processing circuitry.

(17)
The endoscope device according to (12), wherein the processing circuitry is further configured to instruct the illumination device to change an illumination direction.

(18)
The endoscope device according to (17), wherein the processing circuitry is further configured to instruct the illumination device to change the illumination direction in response to a frame being output by the processing circuitry.

(19)
The endoscope device according to (17), wherein the processing circuitry is further configured to instruct the illumination device to change the illumination direction in response to at least two frames being output by the processing circuitry.

(20)
The endoscope device according to (12)-(19), wherein the processing circuitry is further configured to perform image processing on the composite image generated from the combining of the at least two obtained frames.

(21)
The endoscope device according to (12), wherein the illumination state is changed by a movement of a body of a patient.

(22)
An image processing method for processing image data obtained from an endoscope device configured to output the image data, including obtaining, from the image data, at least two frames each captured with a different illumination state, generating, from the at least two obtained frames, a composite image that has a reduced specular reflection light component with respect to at least one of the obtained frames, and generating a video signal including the composite image.

(23)

An image processing device including:

a signal processing unit configured to compose a first photograph image obtained by photographing a living body irradiated with illumination light in a first illumination direction and a second photograph image obtained by photographing the living body irradiated with illumination light in a second illumination direction to generate a composite image.

(24)

The image processing device according to (23), further including:

an illumination control unit configured to control an illumination unit that emits the illumination light.

(25)

The image processing device according to (24), wherein the illumination control unit controls the illumination unit so as to switch an illumination direction of the illumination light to the first illumination direction or the second illumination direction.

(26)

The image processing device according to (24), wherein the illumination control unit controls the illumination unit so as to turn on or off each of the illumination light in the first illumination direction and the illumination light in the second illumination direction.

(27)

The image processing device according to any of (23) to (26), wherein the illumination light is emitted from an endoscope that photographs the living body.

(28)

The image processing device according to any of (23) to (27), wherein the illumination light is emitted from an external tool that is different from an endoscope that photographs the living body.

(29)

The image processing device according to any of (23) to (28), wherein the first photograph image is an image obtained by irradiating the living body with illumination light in the first illumination direction toward a central part of the living body projected on the first photograph image, and wherein the second photograph image is an image obtained by irradiating the living body with illumination light in the second illumination direction toward a peripheral part of the living body projected on the second photograph image.

(30)

The image processing device according to any of (23) to (29), wherein the first photograph image is an image of one of an odd-numbered frame and an even-numbered frame, and wherein the second photograph image is an image of the other one of the odd-numbered frame and the even-numbered frame.

(31)

The image processing device according to (30), wherein the signal processing unit repeats composition of the first photograph image of a first frame and the second photograph image of a second frame subsequent to the first frame, and composition of the first photograph image of a third frame subsequent to the second frame and the second photograph image of a fourth frame subsequent to the third frame.

(32)

The image processing device according to (30), wherein the signal processing unit repeats composition of the first photograph image of a first frame and the second photograph image of a second frame subsequent to the first frame, and composition of the second photograph image of the second frame and the first photograph image of a third frame subsequent to the second frame.

(33)

The image processing device according to any of (23) to (32), wherein, in the case where an amount of exposure of a pixel in an attention position of the first photograph image is larger than an amount of exposure of a pixel in the attention position of the second photograph image, the signal processing unit obtains a pixel value of the pixel in the attention position of the first photograph image as a pixel value of a pixel in the attention position of the composite image when the pixel value of the pixel in the attention position of the first photograph image is smaller than a threshold, and obtains a pixel value of the pixel in the attention position of the second photograph image as the pixel value of the pixel in the attention position of the composite image when the pixel value of the pixel in the attention position of the first photograph image is not smaller than the threshold, and in the case where the amount of exposure of the pixel in the attention position of the first photograph image is not larger than the amount of exposure of the pixel in the attention position of the second photograph image, the signal processing unit obtains the pixel value of the pixel in the attention position of the second photograph image as the pixel value of the pixel in the attention position of the composite image when the pixel value of the pixel in the attention position of the second photograph image is smaller than the threshold, and obtains the pixel value of the pixel in the attention position of the first photograph image as the pixel value of the pixel in the attention position of the composite image when the pixel value of the pixel in the attention position of the second photograph image is not smaller than the threshold.

(34)

The image processing device according to (23), wherein the signal processing unit obtains, as a pixel value of a pixel in an attention position of the composite image, a weighting addition value of a pixel value of a pixel in the attention position of the first photograph image and a pixel value of a pixel in the attention position of the second photograph image.

(35)

The image processing device according to (34), wherein the signal processing unit sets weight to be used for obtaining the weighting addition value on the basis of the pixel value of the pixel in the attention position of the first photograph image or the second photograph image.

(36)

The image processing device according to (35), wherein the signal processing unit sets the weight in accordance with the pixel value of the pixel in the attention position of the first photograph image in the case where an amount of exposure of the pixel in the attention position of the first photograph image is larger than an amount of exposure of the pixel in the attention position of the second photograph image, and sets the weight in accordance with the pixel value of the pixel in the attention position of the second photograph image in the case where the amount of exposure of the pixel in the attention position of the first photograph image is not larger than the amount of exposure of the pixel in the attention position of the second photograph image.

(37)

The image processing device according to (36), wherein the signal processing unit obtains a pixel value C of the pixel in the attention position of the composite image in accordance with a formula C=a*Vc+(1−a)*Vo, where Vc indicates a pixel value of a pixel in the attention position of the first photograph image, Vo indicates a pixel value of a pixel in the attention position of the second photograph image, and a indicates weight, sets the weight a that is decreased with respect to increase in the pixel value Vc of the pixel in the attention position of the first photograph image in the case where the amount of exposure of the pixel in the attention position of the first photograph image is larger than the amount of exposure of the pixel in the attention position of the second photograph image, and sets the weight a that is increased with respect to increase in the pixel value Vo of the pixel in the attention position of the second photograph image in the case where the amount of exposure of the pixel in the attention position of the first photograph image is not larger than the amount of exposure of the pixel in the attention position of the second photograph image.

(38)

The image processing device according to any of (23) to (37), wherein the signal processing unit multiplies a pixel value of each pixel of the first photograph image by a gain corresponding to an amount of exposure of the pixel and multiplies a pixel value of each pixel of the second photograph image by a gain corresponding to an amount of exposure of the pixel, and composes the first photograph image and the second photograph image to which the gains have been multiplied.

(39)

The image processing device according to (37), wherein the signal processing unit compresses tones of the composite image generated by composing the first photograph image and the second photograph image to which the gains have been multiplied.

(40)

An image processing method including:

composing a first photograph image obtained by photographing a living body irradiated with illumination light in a first illumination direction and a second photograph image obtained by photographing the living body irradiated with illumination light in a second illumination direction to generate a composite image.

(41)

A program for causing a computer to function as:

a signal processing unit configured to compose a first photograph image obtained by photographing a living body irradiated with illumination light in a first illumination direction and a second photograph image obtained by photographing the living body irradiated with illumination light in a second illumination direction to generate a composite image.

(42)

An endoscope system including:

an endoscope configured to photograph a living body;

a signal processing unit configured to compose a first photograph image obtained by photographing a living body irradiated with illumination light in a first illumination direction with the use of the endoscope and a second photograph image obtained by photographing the living body irradiated with illumination light in a second illumination direction with the use of the endoscope to generate a composite image; and a display unit configured to display the composite image.

REFERENCE SIGNS LIST 11 endoscope
11A image sensor
12 memory
13 signal processing unit
14 display unit
15 photographing control unit
16 illumination control unit
17 illumination unit
21 camera head
22 endoscope scope
31 forceps
32 surgical part
101 bus
102 CPU
103 ROM
104 RAM
105 hard disk
106 output unit
107 input unit
108 communication unit
109 drive
110 input/output interface
111 removable recording medium

The invention claimed is:

1. An endoscopic system comprising:
an endoscope device configured to output image data having a plurality of frames output at a frame rate;
an illumination device configured to illuminate a body of a patient, the illumination device comprising an illumination window capable of emitting light; and
circuitry configured to
obtain, from the plurality of frames in the image data, at least two frames each captured with a different illumination state,
in a case that an even-numbered frame is obtained, control a direction of light emitted from the illumination window to be one of a peripheral direction or a central direction, and
in a case that an odd-numbered frame is obtained, control the direction of the light emitted from the illumination window to be an other one of the peripheral direction or the central direction, such that the direction of the light emitted is different for the odd-numbered frame and the even-numbered frame,
generate, from the even-numbered frame and the odd-numbered frame, a composite image that has a reduced specular reflection light component with respect to at least one of the obtained frames, and
generate a video signal having the frame rate and including the composite image.

2. The endoscopic system according to claim 1, wherein the illumination device is configured to illuminate the body of the patient from different illumination positions to change the illumination state.

3. The endoscopic system according to claim 1, wherein the circuitry is further configured to instruct the illumination device to change an illumination direction.

4. The endoscopic system according to claim 3, wherein the circuitry is further configured to instruct the illumination device to change the illumination direction in response to a frame being output by the endoscope device.

5. The endoscopic system according to claim 3, wherein the circuitry is further configured to instruct the illumination device to change the illumination direction in response to at least two frames being output by the endoscope device.

6. The endoscopic system according to claim 1, wherein the illumination state is changed by a movement of the body of the patient.

7. The endoscopic system according to claim 1, further comprising:
a trocar configured to permit insertion of the illumination device in the body of the patient.

8. The endoscopic system according to claim 1, wherein the circuitry is further configured to perform image processing on the composite image generated from the at least two obtained frames.

9. The endoscopic system according to claim 1, wherein the circuitry is further configured to control the direction of light emitted by rotating the illumination window of the endoscopic device.

10. An image processing apparatus, comprising:
processing circuitry configured to
control a direction of light emitted from an illumination device comprising an illumination window capable of emitting light,
obtain, from the image data having a plurality of frames output from an endoscope at a frame rate, at least two frames each captured with a different illumination state,
in a case that an even-numbered frame is obtained, control a direction of light emitted from the illumination window to be one of a peripheral direction or a central direction, and
in a case that an odd-numbered frame is obtained, control the direction of the light emitted from the illumination window to be an other one of the peripheral direction or the central direction, such that the direction of the light emitted is different for the odd-numbered frame and the even-numbered frame,
generate, from the even-numbered frame and the odd-numbered frame, a composite image that has a reduced specular reflection light component with respect to at least one of the obtained frames, and
generate a video signal having the frame rate and including the composite image.

11. The image processing apparatus according to claim 10, wherein the processing circuitry is further configured to instruct the illumination device to change an illumination position.

12. The image processing apparatus according to claim 11, wherein the processing circuitry is further configured to instruct the illumination device to change the illumination position in response to a frame being output by the processing circuitry.

13. The image processing apparatus according to claim 10, wherein the processing circuitry is further configured to instruct the illumination device to change an illumination direction.

14. The image processing apparatus according to claim 13, wherein the processing circuitry is further configured to instruct the illumination device to change the illumination direction in response to a frame being output by the processing circuitry.

15. The image processing apparatus according to claim 13, wherein the processing circuitry is further configured to instruct the illumination device to change the illumination direction in response to at least two frames being output by the processing circuitry.

16. The image processing apparatus according to claim 10, wherein the processing circuitry is further configured to perform image processing on the composite image generated from the at least two obtained frames.

17. The image processing apparatus according to claim 10, wherein the illumination state is changed by a movement of a body of a patient.

18. An image processing method for processing image data having a plurality of frames obtained at a frame rate from an endoscope device configured to output the image data, comprising:
controlling a direction of light emitted from an illumination device comprising an illumination window,
obtaining, from the plurality of frames in the image data, at least two frames each captured with a different illumination state,
in a case that an even-numbered frame is obtained, control a direction of light emitted from the illumination window to be one of a peripheral direction or a central direction, and
in a case that an odd-numbered frame is obtained, control the direction of the light emitted from the illumination window to be an other one of the peripheral direction or the central direction, such that the direction of the light emitted is different for the odd-numbered frame and the even-numbered frame,
generating, from the even-numbered frame and the odd-numbered frame, a composite image that has a reduced specular reflection light component with respect to at least one of the obtained frames, and
generating a video signal having the frame rate and including the composite image.

* * * * *